(12) United States Patent
Sporbert et al.

(10) Patent No.: US 9,572,636 B2
(45) Date of Patent: Feb. 21, 2017

(54) METHOD AND SYSTEM FOR FINDING TOOTH FEATURES ON A VIRTUAL THREE-DIMENSIONAL MODEL

(71) Applicant: OraMetrix, Inc., Richardson, TX (US)

(72) Inventors: Peer Sporbert, Berlin (DE); Hans Imgrund, Berlin (DE); Markus Kaufmann, Berlin (DE)

(73) Assignee: ORAMETRIX, INC., Richardson, TX (US)

( * ) Notice: Subject to any disclaimer, the term of this patent is extended or adjusted under 35 U.S.C. 154(b) by 430 days.

(21) Appl. No.: 14/134,021

(22) Filed: Dec. 19, 2013

(65) Prior Publication Data
US 2015/0173855 A1    Jun. 25, 2015

(51) Int. Cl.
| | |
|---|---|
| *G06F 17/50* | (2006.01) |
| *A61C 7/00* | (2006.01) |
| *A61C 9/00* | (2006.01) |
| *G06T 19/00* | (2011.01) |
| *A61C 7/14* | (2006.01) |
| *A61C 13/00* | (2006.01) |

(52) U.S. Cl.
CPC .............. *A61C 7/002* (2013.01); *A61C 7/00* (2013.01); *A61C 9/0046* (2013.01); *A61C 9/0053* (2013.01); *G06F 17/50* (2013.01); *G06T 19/003* (2013.01); *A61C 7/146* (2013.01); *A61C 13/0004* (2013.01); *A61C 2007/004* (2013.01)

(58) Field of Classification Search
CPC ... A61C 7/0002; A61C 9/0053; A61C 9/0046; A61C 7/00; A61C 7/146; A61C 2007/004; A61C 13/0004; G06F 17/50; G06T 19/003
USPC .......................................................... 703/1
See application file for complete search history.

(56) References Cited

U.S. PATENT DOCUMENTS

2006/0263739 A1\* 11/2006 Sporbert .................. A61C 7/00
433/24

\* cited by examiner

*Primary Examiner* — Dwin M Craig
(74) *Attorney, Agent, or Firm* — Jasvantrai C. Shah

(57) ABSTRACT

A method and system are disclosed for finding virtual tooth features on virtual three-dimensional models of the teeth of patients. The tooth features comprise marginal ridges, cusp tips, contact points, central groove and buccal groove. Tooth axes system plays a key role in identifying the tooth features. An iterative method is disclosed for improving the accuracy of the tooth axes system. A virtual three-dimension model preferably obtained by scanning the dentition of a patient forms the basis for determining the tooth features. Tooth features are derived for all categories of teeth including molars, premolars, canines and front teeth. Tooth features are very helpful and used in planning orthodontic treatment. The tooth features are determined automatically using the computerized techniques; and can be manually adjusted when necessary.

6 Claims, 33 Drawing Sheets

METHOD AND SYSTEM FOR FINDING TOOTH FEATURES ON A VIRTUAL THREE-DIMENSIONAL MODEL

CROSS-REFERENCE TO RELATED APPLICATIONS

This is a continuation application of Ser. No. 12/713,169, which is a divisional application of Ser. No. 11/233,623, filed Sep. 23, 2005, now issued as U.S. Pat. No. 7,695,278, which is a continuation-in-part of application entitled "METHOD AND SYSTEM FOR COMPREHENSIVE EVALUATION OF ORTHODONTIC CARE USING UNIFIED WORKSTATION," Ser. No. 11/133,996, filed May 20, 2005, now issued as U.S. Pat. No. 8,021,147, the entire contents of which are incorporated by reference herein.

BACKGROUND OF THE INVENTION

A. Field of the Invention

This invention relates to the field of computerized techniques for orthodontic treatment planning for human patients. More particularly, the invention is directed to finding virtual tooth features, which are very helpful and used in planning orthodontic treatment, on a virtual three-dimensional model of dentition. The tooth features are determined automatically using the computerized techniques; and can be manually adjusted when necessary.

B. Description of Related Art

The traditional process of diagnosis and treatment planning for a patient with orthodontic problems or disease typically consists of the practitioner obtaining clinical history, medical history, dental history, and orthodontic history of the patient supplemented by 2D photographs, 2D radiographic images, CT scans, 2D and 3D scanned images, ultrasonic scanned images, and in general non-invasive and sometimes invasive images, plus video, audio, and a variety of communication records. Additionally, physical models, such as made from plaster of paris, of the patient's teeth are created from the impressions taken of the patient's upper and lower jaws. Often, such models are manually converted into teeth drawings by projecting teeth on drawing paper. Thus, there is a large volume of images and data involved in the diagnosis and treatment planning process. Furthermore, the information may require conversion from one form to another and selective reduction before it could become useful. There are some computerized tools available to aid the practitioner in these data conversion and reduction steps, for example to convert cephalometric x-rays (i.e., 2 dimensional x-ray photographs showing a lateral view of the head and jaws, including teeth) into points of interest with respect to soft tissue, hard tissue, etc., but they are limited in their functionalities and scope. Even then, there is a fairly substantial amount of manual work involved in these steps.

Consequently, the practitioner is left to mental visualization, chance process to select the treatment course that would supposedly work. Furthermore, the diagnosis process is some-what ad-hoc and the effectiveness of the treatment depends heavily upon the practitioner's level of experience. Often, due to the complexities of the detailed steps and the time consuming nature of them, some practitioners take a shortcut, relying predominantly on their intuition to select a treatment plan. For example, the diagnosis and treatment planning is often done by the practitioner on a sheet of acetate placed over the X-rays. All of these factors frequently contribute towards trial and error, hit-and-miss, lengthy and inefficient treatment plans that require numerous mid-course adjustments. While at the beginning of treatment things generally run well as all teeth start to move at least into the right direction, at the end of treatment a lot of time is lost by adaptations and corrections required due to the fact that the end result has not been properly planned at any point of time. By and large, this approach lacks reliability, reproducibility and precision. More over, there is no comprehensive way available to a practitioner to stage and simulate the treatment process in advance of the actual implementation to avoid the often hidden pitfalls. And the patient has no choice and does not know that treatment time could be significantly reduced if proper planning was done.

In recent years, computer-based approaches have been proposed for aiding orthodontists in their practice. See Andreiko, U.S. Pat. No. 6,015,289; Snow, U.S. Pat. No. 6,068,482; Kopelmann et al., U.S. Pat. No. 6,099,314; Doyle, et al., U.S. Pat. No. 5,879,158; Wu et al., U.S. Pat. No. 5,338,198, and Chisti et al., U.S. Pat. Nos. 5,975,893 and 6,227,850, the contents of each of which is incorporated by reference herein. Also see imaging and diagnostic software and other related products marketed by Dolphin Imaging, 6641 Independence Avenue, Canoga Park, Calif. 91303-2944.

U.S. Pat. No. 6,648,640 to Rubbert, et al. describes an interactive, computer based orthodontist treatment planning, appliance design and appliance manufacturing. A scanner is described which acquires images of the dentition, which are converted to three-dimensional frames of data. The data from the several frames are registered to each other to provide a complete three-dimensional virtual model of the dentition. Individual tooth objects are obtained from the virtual model. A computer-interactive software program provides for treatment planning, diagnosis and appliance design from the virtual tooth models. A desired occlusion for the patient is obtained from the treatment planning software. The virtual model of the desired occlusion and the virtual model of the original dentition provide a base of information for custom manufacture of an orthodontic appliance. A variety of possible appliance and appliance manufacturing systems are contemplated, including customized arch wires and customized devices for placement of off-the shelf brackets on the patient's dentition for housing the arch wires, and removable orthodontic appliances.

U.S. Pat. No. 6,632,089 to Rubbert, et al. describes an interactive, software-based treatment planning method to correct a malocclusion. The method can be performed on an orthodontic workstation in a clinic or at a remote location such as a lab or precision appliance-manufacturing center. The workstation stores a virtual three-dimensional model of the dentition of a patient and patient records. The virtual model is manipulated by the user to define a target situation for the patient, including a target arch-form and individual tooth positions in the arch-form. Parameters for an orthodontic appliance, such as the location of orthodontic brackets and resulting shape of an orthodontic arch wire, are obtained from the simulation of tooth movement to the target situation and the placement position of virtual brackets. The treatment planning can also be executed remotely by a precision appliance service center having access to the virtual model of the dentition. In the latter situation, the proposed treatment plan is sent to the clinic for review, and modification or approval by the orthodontist. The method is suitable for other orthodontic appliance systems, including removable appliances such as transparent aligning trays.

Other background references related to capturing three dimensional models of dentition and associated craniofacial structures include S. M. Yamany and A. A. Farag, "A System for Human Jaw Modeling Using Intra-Oral Images" in *Proc. IEEE Eng. Med. Biol. Soc. (EMBS) Conf.*, Vol. 20, Hong Kong, October 1998, pp. 563-566; and M. Yamany, A. A. Farag, David Tasman, A. G. Farman, "A 3-D Reconstruction System for the Human Jaw Using a Sequence of Optical Images," *IEEE Transactions on Medical Imaging*, Vol. 19, No. 5, May 2000, pp. 538-547. The contents of these references are incorporated by reference herein.

The technical literature further includes a body of literature describing the creation of 3D models of faces from photographs, and computerized facial animation and morphable modeling of faces. See, e.g., Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of 3D Faces*, Computer Graphics Proceedings SIGGRAPH '99 (August, 1999). The contents of these references are incorporated by reference herein.

Tooth features, such as the cusp tips, marginal ridges, central groove lines, buccal grooves, contact points, tooth axes system, etc. play key roles in defining some well established orthodontic treatment planning criteria such as: alignment, marginal ridges, buccolingual inclination, occlusal relationships, occlusal contacts, overjet, interproximal contacts, root angulation, etc. Indeed, the American Board of Orthodontics (ABO) has introduced an Objective Grading System (OGS) for evaluating the results of an orthodontic treatment once it is completed using these criteria. Alignment refers to an assessment of tooth alignment. In the anterior region, the incisal edges and lingual surfaces of the maxillary anterior teeth and the incisal edges and labial-incisal surfaces of the mandibular anterior teeth are chosen to assess anterior alignment. In the maxillary posterior region, the mesiodistal central groove of the premolars and molars is used to assess adequacy of alignment. In the mandibular arch, the buccal cusps of the premolars and molars are used to assess proper alignment. Marginal ridges are used to assess proper vertical positioning of the posterior teeth. If marginal ridges are at the same height, it will be easier to establish proper occlusal contacts, since some marginal ridges provide contact areas for opposing cusps. Buccolingual inclination is used to assess the buccolingual angulation of the posterior teeth. In order to establish proper occlusion in maximum intercuspation and avoid balancing interferences, there should not be a significant difference between the heights of the buccal and lingual cusps of the maxillary and mandibular molars and premolars. Occlusal relationship is used to assess the relative anteroposterior position of the maxillary and mandibular posterior teeth. The buccal cusps of the maxillary molars, premolars, and canines must properly align with the interproximal embrasures of the mandibular posterior teeth. The mesiobuccal cusp of the maxillary first molar must properly align with the buccal groove of the mandibular first molar. Occlusal contacts are measured to assess the adequacy of the posterior occlusion. Again, a major objective of orthodontic treatment is to establish maximum intercuspation of opposing teeth. Therefore, the functioning cusps are used to assess the adequacy of this criterion; i.e., the buccal cusps of the mandibular molars and premolars, and the lingual cusps of the maxillary molars and premolars. Overjet is used to assess the relative transverse relationship of the posterior teeth, and the anteroposterior relationship of the anterior teeth. In the posterior region, the mandibular buccal cusps and maxillary lingual cusps are used to determine proper position within the fossae of the opposing arch. In the anterior region, the mandibular incisal edges should be in contact with the lingual surfaces of the maxillary anterior teeth. Interproximal contacts are used to determine if all spaces within the dental arch have been closed. Persistent spaces between teeth after orthodontic therapy are not only unesthetic, but can lead to food impaction. Root angulation is used to assess how well the roots of the teeth have been positioned relative to one another.

Traditionally, the tooth features discussed above are visually identified and marked by the practitioner; and various measurements related to the treatment criteria are performed manually using measuring instruments and gauges. The ABO has developed an orthodontic measuring gauge to assist in the manual measurement of parameters related to the OGS criteria discussed above from the dental cast and the panoramic radiograph. Although the measuring gauges introduce a degree of consistency in the measurements when performed by different people, the measurements are still limited in scope to two-dimensional analysis.

Therefore, in order to enable computerized orthodontic treatment planning, and three-dimensional, accurate measurements of the criteria such as those developed by ABO, there is a need for digitally finding tooth features, such as the cusp tips, marginal ridges, central groove lines, buccal grooves, contact points, tooth axes system, etc., on a three-dimensional virtual dentition model of a patient.

U.S. Pat. No. 6,616,444 to Andreiko, et al. describes a system and method by which an orthodontic appliance is automatically designed and manufactured from digital lower jaw and tooth shape data of a patient. The method provides for scanning a model of the patient's mouth to produce two or three dimensional images and digitizing contours and selected points. A computer may be programmed to construct archforms and/or to calculate finish positions of the teeth, then to design an appliance to move the teeth to the calculated positions.

U.S. Pat. No. 6,322,359 to Jordan, et al. describes a computer implemented method of creating a dental model for use in dental articulation. The method provides a first set of digital data corresponding to an upper arch image of at least a portion of an upper dental arch of a patient, a second set of digital data corresponding to a lower arch image of at least a portion of a lower dental arch of the patient, and hinge axis data representative of the spatial orientation of at least one of the upper and lower dental arches relative to a condylar axis of the patient. A reference hinge axis is created relative to the upper and lower arch images based on the hinge axis data. Further, the method may include bite alignment data for use in aligning the lower and upper arch images. Yet further, the method may include providing data associated with condyle geometry of the patient, so as to provide limitations on the movement of at least the lower arch image when the arch images are displayed. Further, a wobbling technique may be used to determine an occlusal position of the lower and upper dental arches. Various computer implemented methods of dental articulation are also described. For example, such dental articulation methods may include moving at least one of the upper and lower arch images to simulate relative movement of one of the upper and lower dental arches of the patient, may include displaying another image with the upper and lower dental arches of the dental articulation model, and/or may include playing back recorded motion of a patient's mandible using the dental articulation model.

The invention disclosed herein offers a novel method and system for digitally finding tooth features, such as the cusp tips, marginal ridges, central groove lines, buccal grooves, contact points, tooth axes system, etc., on a three-dimensional virtual dentition model of a patient.

SUMMARY OF THE INVENTION

The invention is directed to finding virtual tooth features on virtual three-dimensional models of teeth. The tooth features comprise marginal ridges, cusp tips, contact points, central groove and buccal groove. A virtual three-dimension model preferably obtained by scanning the dentition of a patient forms the basis for determining the tooth features. Tooth features are derived for all categories of teeth including molars, premolars, canines and front teeth. Tooth features are very helpful and used in planning orthodontic treatment. The tooth features are determined automatically using the computerized techniques; and can be manually adjusted when necessary. The tooth axes system (TAS) plays an important role in determining the tooth features listed above. Indeed, the TAS it self is considered a tooth feature. The TAS is created for each individual tooth based up on the ideal properties of the tooth in terms of its features. TAS is preferably an anatomical coordinate system for the tooth. It is preferably derived during virtual modelling of the tooth from the scanning data using the tooth templates. The TAS for a virtual tooth comprises the origin, the x-axis in the mesial and distal directions, the y-axis in the buccal and lingual directions and the z-axis in the occlusal and gingival (vertical) directions.

In a first aspect of the invention, a method is disclosed for finding the ridge on a virtual three-dimensional model of a molar or a premolar. The ridge comprises a set of outer most points on the occlusal surface of the tooth determined as follows:

(a) a set of sufficient number of curves is produced along the surface of the tooth by intersecting the tooth surface with planes containing the z-axis from the TAS of the virtual tooth;

(b) each curve is then traced starting from the bottom of the tooth (the face opposite to the occlusal surface) first on one side (e.g. left) and then the other side and a ridge point is found on either side such that the tangent to the tooth surface at the ridge point is preferably horizontal or nearly horizontal; and (c) the family of points obtained in this manner forms the ridge for the tooth.

In another aspect of the invention, a method is disclosed for finding the marginal ridges on virtual three-dimensional models of molars and premolars. Two local minima, one at the mesial side of the tooth, and another at the distal side of the tooth are found from the ridge. These two minima are the marginal ridges for the tooth.

In another aspect of the invention, a method is disclosed for finding the cusp tips on virtual three-dimensional models of molars and premolars. The marginal ridges are used to divide the ridge into two subsets, with each subset bounded by the two marginal ridges, one subset at the buccal side of the tooth (the buccal branch), and the other at the lingual side (the lingual branch). Now the local maxima (maximal z-coordinate) of the buccal branch define the buccal cusp tips, and the local maxima of the lingual branch define the lingual cusp tips.

In another aspect of the invention, a method is disclosed for finding the cusp tips on virtual three-dimensional models of canines. The most or highest occlusal point of the virtual tooth model (the point with the highest z-coordinate) is chosen as the cusp tip for a canine tooth.

In another aspect of the invention, a method is disclosed for finding the cusp tips on virtual three-dimensional models of front teeth. For each front tooth, two points of the occlusal lateral edges are defined as the "cusp tips". With regard to these cusp tips, there is a differentiation made between maxilla and mandible front teeth. In the maxilla these two points are situated on the lingual side of the front teeth; while in the mandible they are situated on the labial side of the front teeth. In order to determine these cusp tips, the tooth model is rotated around the tooth TAS origin or any other point in the tooth, first by 45° in a) mesial direction, or b) distal direction; and after that in c) lingual direction, or d) labial direction. This whole procedure is repeated twice, once with direction a), then with direction b). This leads to the two points for the cusp tips. Direction d) is chosen for the maxilla teeth, direction c) for the mandible teeth. After the rotation, the most or highest occlusal point of the rotated tooth model is chosen as a cusp tip.

In another aspect of the invention, a method is disclosed for finding the ideal contact points on virtual three-dimensional models of teeth. The surface of the tooth model is intersected with the x-y plane based up on the TAS for the tooth. Then, the most mesial point and the most distal point (i.e. points with the lowest/highest x-coordinates), are the two ideal contact points for the tooth.

In another aspect of the invention, a method is disclosed for correcting the TAS. TAS plays a key role in identifying the tooth features. An iterative method is disclosed for improving the accuracy of the tooth axes system. The cusp tips are used to correct the TAS for a tooth as follows:

a) If there are at least three cusp tips, then the TAS is rotated in such a way that all cusp tips have (approximately) the same z-coordinate. If there are three cusp tips, they will have exactly the same z-coordinate. On the other hand, if there are more than three cusp tips, then an approximate a solution is found which minimizes the differences of the z-coordinates.

b) If there are two cusp tips (such as in premolars), then the TAS is rotated around an axis, which passes through the origin of the TAS for the tooth and is perpendicular to the z-axis and to the vector connecting the two cusp tips, by an angle such that the z-coordinates of the two cusp tips are equal.

In another aspect, when the TAS is corrected in a manner described above, the ridge, the marginal ridges and the cusp tips are determined again in order to improve the accuracy of the tooth features. Subsequently, the TAS is also refined, and the entire process of refining the tooth features is repeated. The process may be stopped when (a) a limit is reached in the angle of rotation of the correction applied to the TAS, or (b) the maximum iteration count is reached. Alternately, a combination of the iteration stopping criteria (a) and (b) can also be used.

In another aspect of the invention, a method is disclosed for finding the central groove on virtual three-dimensional models of molars and premolars. The most occlusal (i.e. the point having the highest z-coordinate) cusp tips of the lingual side $C^l$ and the buccal side $C^b$ are determined using the procedure described earlier. Then, the tooth is rotated around the TAS x-axis using a rotation matrix, so that $C^l$ and $C^b$ have the same z-coordinates. Next, a plane $E_k$ parallel to the y-z-plane is moved and cut with all edges of the tooth surface which is represented in the form of triangles derived during the registration process of the scanned tooth model, of which both vertex-normals point upwards. Then, the intersection points are sorted along the y-axis. The tooth surface contour shows the typical shape of a molar with two "mountains" and a "valley" (the central groove). From each slice of the tooth surface, the deepest point of the valley is found. The criterion specified above assures that only the edges of the occlusal surface of the tooth are considered. Next, a linear approximation of the points is found, i.e. a (three-dimensional) line, which has minimal average (quadratic) distance to the points. This line does not need to be the exact minimum, an approximation is good enough. Then, the two points $c_0$ and $c_1$ are calculated as the end-points of the central groove of the tooth. It should be noted that these central groove points $c_0$ and $c_1$ are in general not on the surface of the tooth model. Therefore, for proper use of the central groove in treatment planning, the central groove points are put onto the tooth surface. One possibility for accomplishing this is to construct a line through $c_0$ and $c_1$, respectively, parallel to the z-axis of the TAS for the tooth (i.e. the occlusal direction), and cut it with all triangles of the tooth models. Of all intersection points, the most occlusal point (i.e. the point with the greatest z-coordinate) on the surface of the tooth is taken as the point representing the central groove. That is, the procedure is done once for $c_0$ and again for $c_1$.

In another aspect of the invention, a method is disclosed for finding the buccal groove on virtual three-dimensional models of molar. The procedure is summarized as follows:

Step 1. Let $\tilde{C}_M$ be the mesial labial cusp tip of the tooth-model of interest, and $\tilde{C}_D$ the distal labial cusp tip. Then, find the two closest vertices $C_M$ and $C_D$.

Step 2. Rotate the tooth-model around its x-axis (torque it) lingually by 60°.

Step 3. After this rotation, rotate the tooth-model around an axis, which is orthogonal to the z-axis and to the vector connecting the two cusps $C_M$ and $C_D$ so that the two cusps have the same z-coordinate. Move the cusp tips along the tooth-surface, until they are on local maxima, and repeat rotation for each iteration of Step 3.

a) Perform rotation;

b) Choose one of the two cusp tips, which has been moved less up to now (or any, if they have been moved equally).

c) Let N(C) be the neighborhood of C, i.e. all vertices of the tooth model, which share an edge with C. From N(C), select a vertex C' with, i.e. the neighboring point of C, which has the greatest z-coordinate after applying the transformation. If $C'_z \leq C_z$, this means that C is already a local maximum. In this case choose the other cusp (that means, now C will stand for $C_D$ if it stood for $C_M$ before and vice versa), and repeat step c). If both cusps are local maxima, then step 3) is finished; and go to step 4).

d) replace C by C' and go back to a).

Step 4. Find a "saddle-point" (the "lowest" vertex along the "highest" path from cusp to cusp):

(that means, always take the point with the greatest z-coordinate (after applying the transformation) of all vertices, which meet iii) and iv))

From this path, choose the vertex S with the smallest z-coordinate. Then, S is the buccal groove of the tooth model under consideration.

The path, which connects the "moved cusp tips", located at the end-points of the path. The path is the highest possible path, which connects the cusp tips. The lowest point along this path is the "saddle-point", which is the buccal grove of the virtual tooth.

BRIEF DESCRIPTION OF THE DRAWINGS

Presently preferred embodiments of the invention are described below in reference to the appended drawings, wherein like reference numerals refer to like elements in the various views, and in which:

In FIG. 16, the tooth was rotated by 45° to distal direction and 45° to labial direction. In this situation the left cusp tip was found as the most occlusal point.

DETAILED DESCRIPTION OF PREFERRED EMBODIMENTS

Overview

Figure 1:
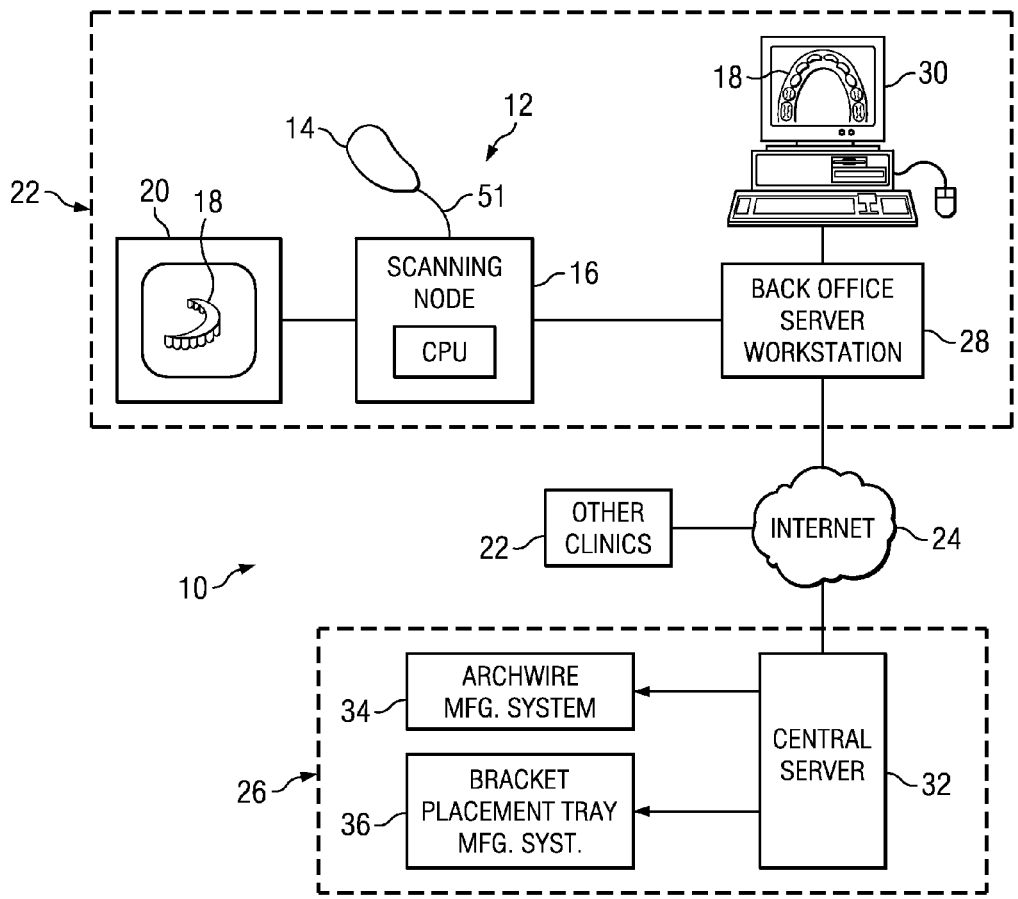
FIG. 1 is an illustration of an orthodontic care system incorporating a hand-held scanner system. The hand-held scanner is used by the orthodontist or the assistant to acquire three-dimensional information of the dentition and associated anatomical structures of a patient and provide a base of information to diagnose and plan treatment for the patient.

FIG. 1 is an illustration of an orthodontic care system 10 incorporating a scanner system 12. The scanner system 12 includes a hand-held scanner 14 that is used by the orthodontist or his assistant to acquire three-dimensional information of the dentition and associated anatomical structures of a patient. The images are processed in a scanning node or workstation 16 having a central processing unit, such as a general-purpose computer. The scanning node 16, either alone or in combination with a back-office server 28, generates a three-dimensional computer model 18 of the dentition and provides the orthodontist with a base of information for diagnosis, planning treatment, and monitoring care for the patient. The model 18 is displayed to the user on a monitor 20 connected to the scanning node 16.

As noted above, the scanner system 12 described in detail herein is optimized for in-vivo scanning of teeth, or alternatively, scanning a plaster model of the teeth and/or an impression of the teeth.

The orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server work station 28 having its own user interface, including a monitor 30. The back office server 28 executes an orthodontic treatment planning software program. The software obtains the three-dimensional digital data of the patient's teeth from the scanning node 16 and displays the model 18 for the orthodontist. The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and design a customized archwire for the patient given the selected bracket positions. When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22.

As shown in FIG. 1, the precision appliance service center 26 includes a central server 32, an arch wire manufacturing system 34 and a bracket placement manufacturing system 36. For more details on these aspects of the illustrated orthodontic care system, the interested reader is directed to the patent application of Rüdger Rubbert et al., filed Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, now issued as U.S. Pat. No. 6,648,640, the entire contents of which are incorporated by reference herein.

Capture of Image Information

Figure 2:
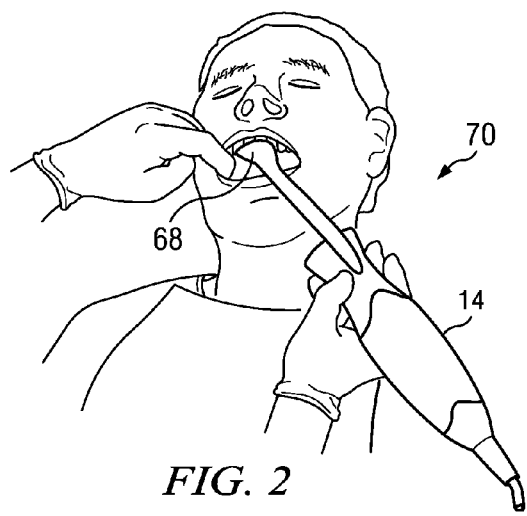
FIG. 2 is an illustration of a patient being scanned with a hand-held scanner.

FIG. 2 is an illustration of a patient 70 being scanned with the hand-held scanner 14. The checks and lips are retracted from the teeth and the tip 68 of the scanner is moved over all the surfaces of the teeth in a sweeping motion. The entire upper or lower jaw may need to be scanned in a series of scans. While FIG. 2 illustrates in-vivo scanning of a human patient, the scanner can of course be used to scan a plaster model of the dentition if that is preferred, or an impression taken from the patient. It is also possible that a scan of a patient may be partially taken in vivo and the remainder from a model or an impression.

Basically, during operation of the scanner to scan an object of unknown surface configuration, hundreds or thousands of images are generated of the projection pattern as reflected off of the object in rapid succession as the scanner and the object are moved relative to each other. For each image, pixel locations for specific portions, i.e., points, of the reflected pattern are compared to entries in the scanner calibration table. X, Y and Z coordinates (i.e., three dimensional coordinates) are obtained for each of these specific portions of the reflected pattern. For each picture, the sum total of all of these X, Y and Z coordinates for specific points in the reflected pattern comprise a three-dimensional "frame" or virtual model of the object. When hundreds or thousands of images of the object are obtained from different perspectives, as the scanner is moved relative to the object, the system generates hundreds or thousands of these frames. These frames are then registered to each other to thereby generate a complete and highly accurate three-dimensional model of the object. The scanning and the registration processes are described in detail in the patent application of Rüdger Rubbert, et al., filed Apr. 13, 2001, entitled METHODS FOR REGISTRATION OF THREE-DIMENSIONAL FRAMES TO CREATE THREE-DIMENSIONAL VIRTUAL MODELS OF OBJECTS, Ser. No. 09/835,007, pending, the entire contents of which are incorporated by reference herein.

Figure 3A:
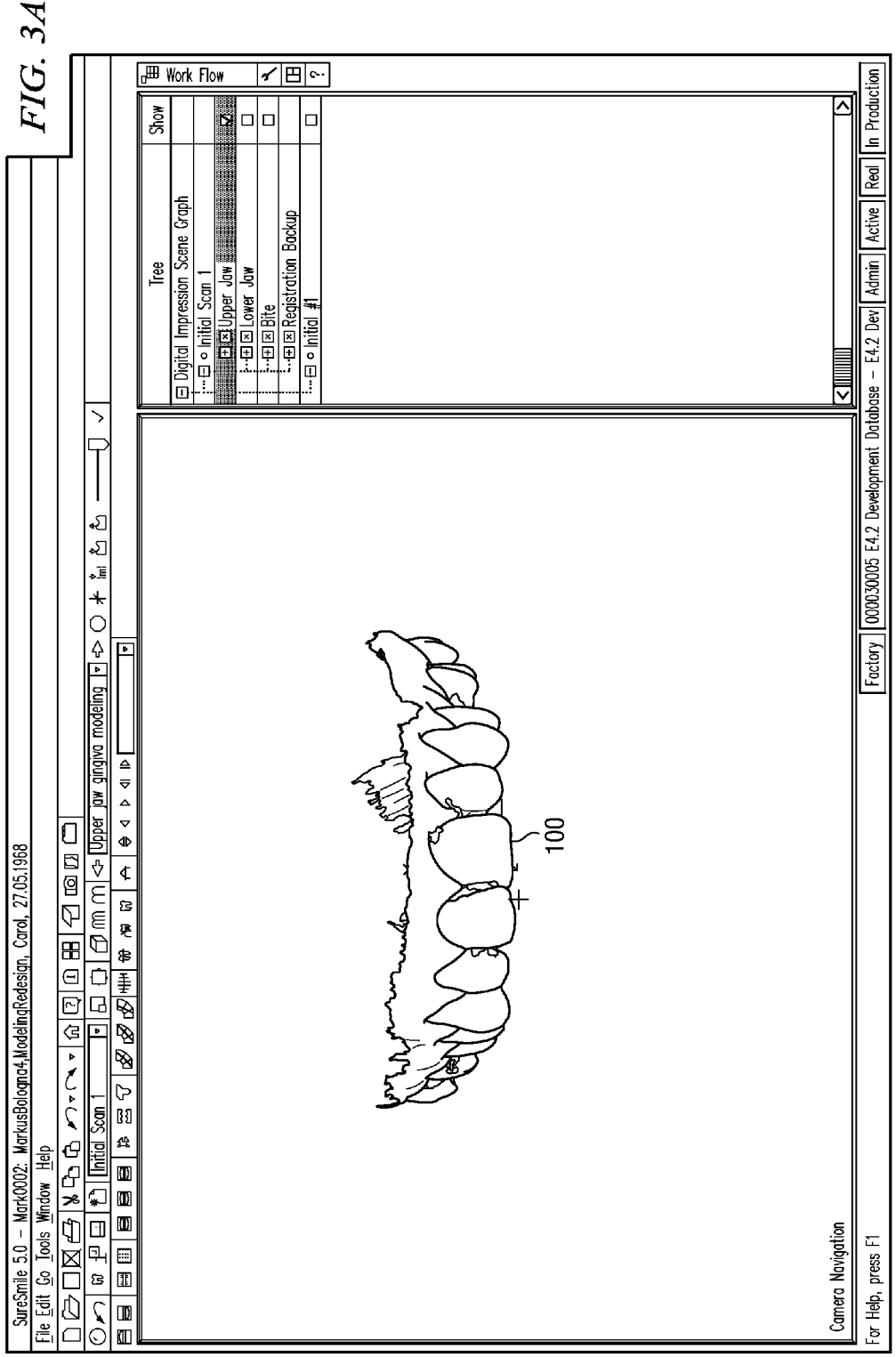
FIGS. 3A and 3B display a front view and an occlusal view, respectively, of a three-dimensional model of the complete maxilla dentition of a patient created by the scanning and registration process.

FIG. 3A displays a front view of a three-dimensional model of the upper jaw 100 of the dentition of a patient created through the scanning and registration process described above.

Figure 3B:
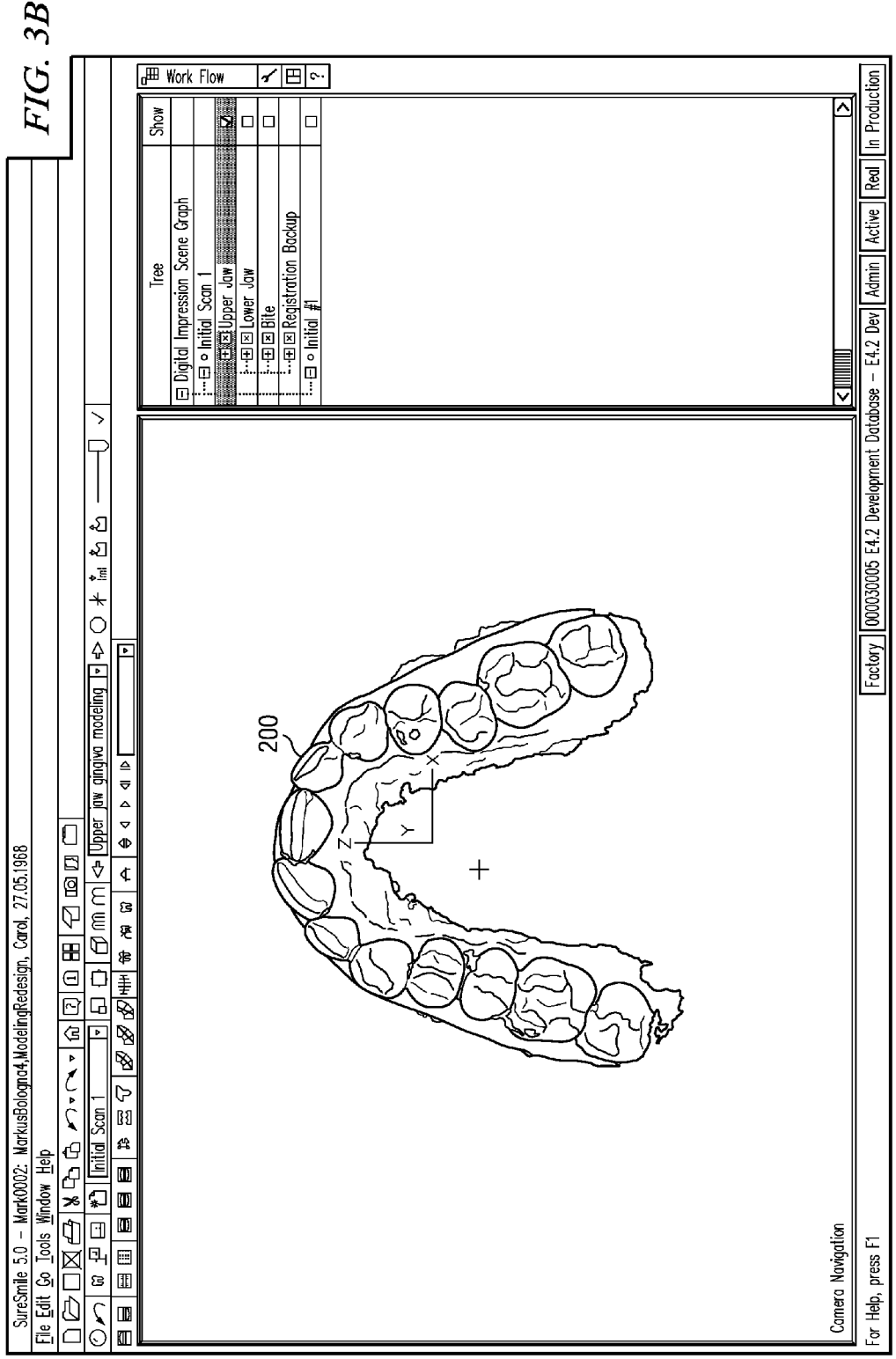

FIG. 3B displays an occlusal view 200 of the three-dimensional model of the upper jaw shown in FIG. 3A.

Separation of Teeth into Individual Tooth Objects (Tooth Modeling)

FIGS. 4A-4F are a series of illustrations showing the generation of an individual tooth model from a scanned tooth. The process is summarized below.

Figure 4A:
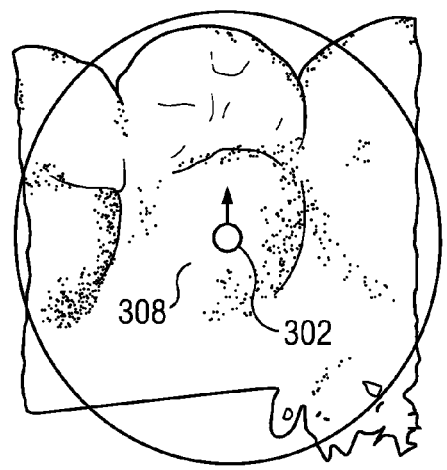
FIG. 4A-4F are a series of illustrations showing the generation of an individual tooth model from a scanned tooth, shown in FIG. 4A, and a template tooth, shown in FIG. 4B. A library of template teeth similar to FIG. 4A are stored as three-dimensional computer models in computer memory. The individual tooth model is a three-dimensional tooth object having a single set of points defining the boundaries of the tooth. Individual tooth models are also invaluable in interactive orthodontic treatment planning since they can be independently moved relative to each other in simulation of treatment scenarios.
Figure 4B:
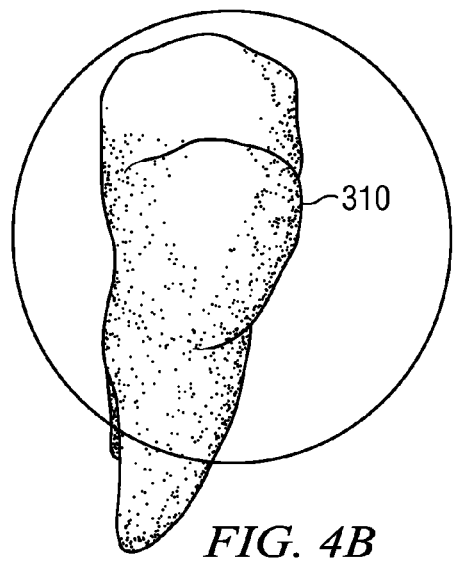
Figure 4C:
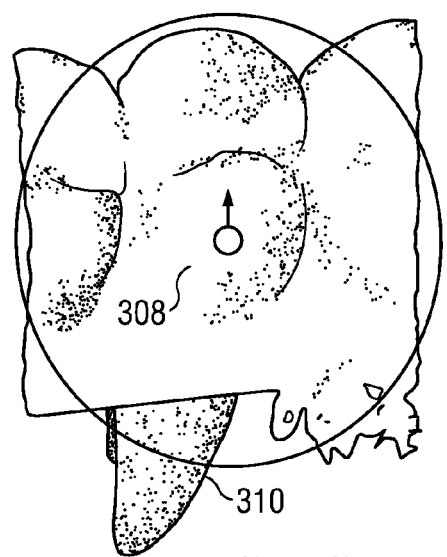

FIG. 4A shows the scanned dentition and associated anatomical structure surrounding the tooth 308. The back office server workstation stores a three-dimensional virtual template tooth object for each tooth in the maxilla and the mandible. The template tooth 310 for the tooth number 308 is shown in FIG. 4B. The template tooth object 310 is a three-dimensional tooth object having a single set of points defining the boundaries of the tooth. As shown in FIG. 4C, the template tooth 310 is positioned approximately in the same location in space as the tooth 308. The landmark 302 assists in providing the proper axial rotation of the template tooth to have it fit properly with respect to the tooth 308. The template tooth is placed at the point cloud of the dentition according to the labial landmark 302. The template tooth can be scaled larger or smaller or positioned arbitrarily by the user, in order to get a close a position as possible to the point cloud of the dentition.

Figure 4D:
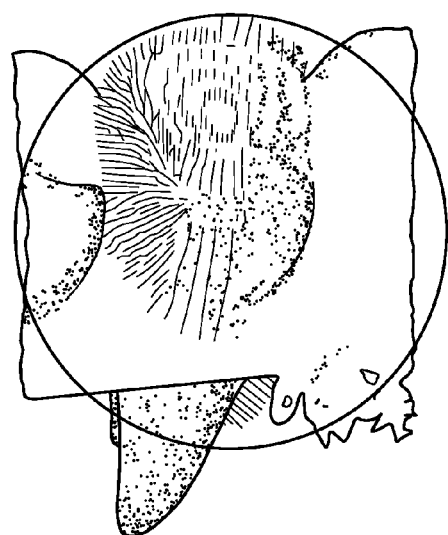
Figure 4E:
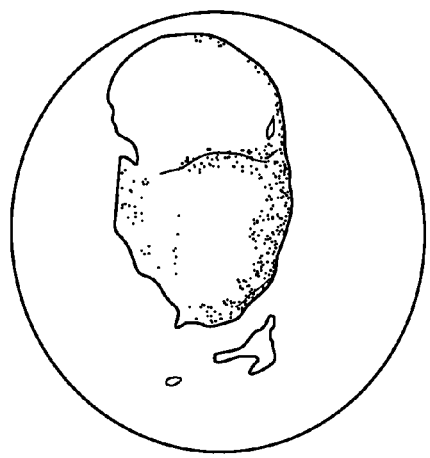
Figure 4F:
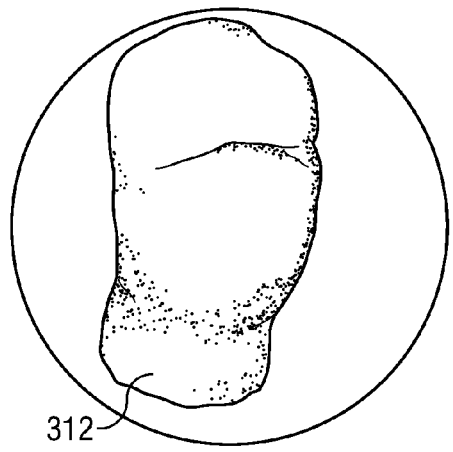

As shown in FIG. 4D, vectors are drawn from the points on the template tooth to the scanned point cloud of the tooth 308. Every ray intersects several surfaces, depending on how often the respective part of the surface has been covered during scanning. For each vector, a surface is selected. Preferably, the smallest triangle surface is selected, since this surface corresponds to an image taken by the scanner when the scanner was positioned in a more perpendicular orientation to the dentition surface, resulting in more accuracy in the determination of the coordinates of that portion of the surface. As another possibility, the outermost surface is selected, using a filter to insure that no extraneous surfaces are used. These points of the surfaces intersected by all the vectors are combined as newly generated triangle surfaces and therefore form one consistent surface shown in FIG. 4E. Then, finally, missing parts of the tooth are completed from the template tooth. The result is shown in FIG. 4F. In a second pass, this generated object is then used as a template tooth, and the steps indicated by FIGS. 4C-4F are repeated in an iterative fashion. This is done to make sure that the algorithm works even if there are significant differences between the original template tooth and the scanned point cloud, e.g, a gap in scan data, different geometry in the tooth. The goal is to provide an algorithm that does not require a closely fitting template tooth object.

Figure 5:
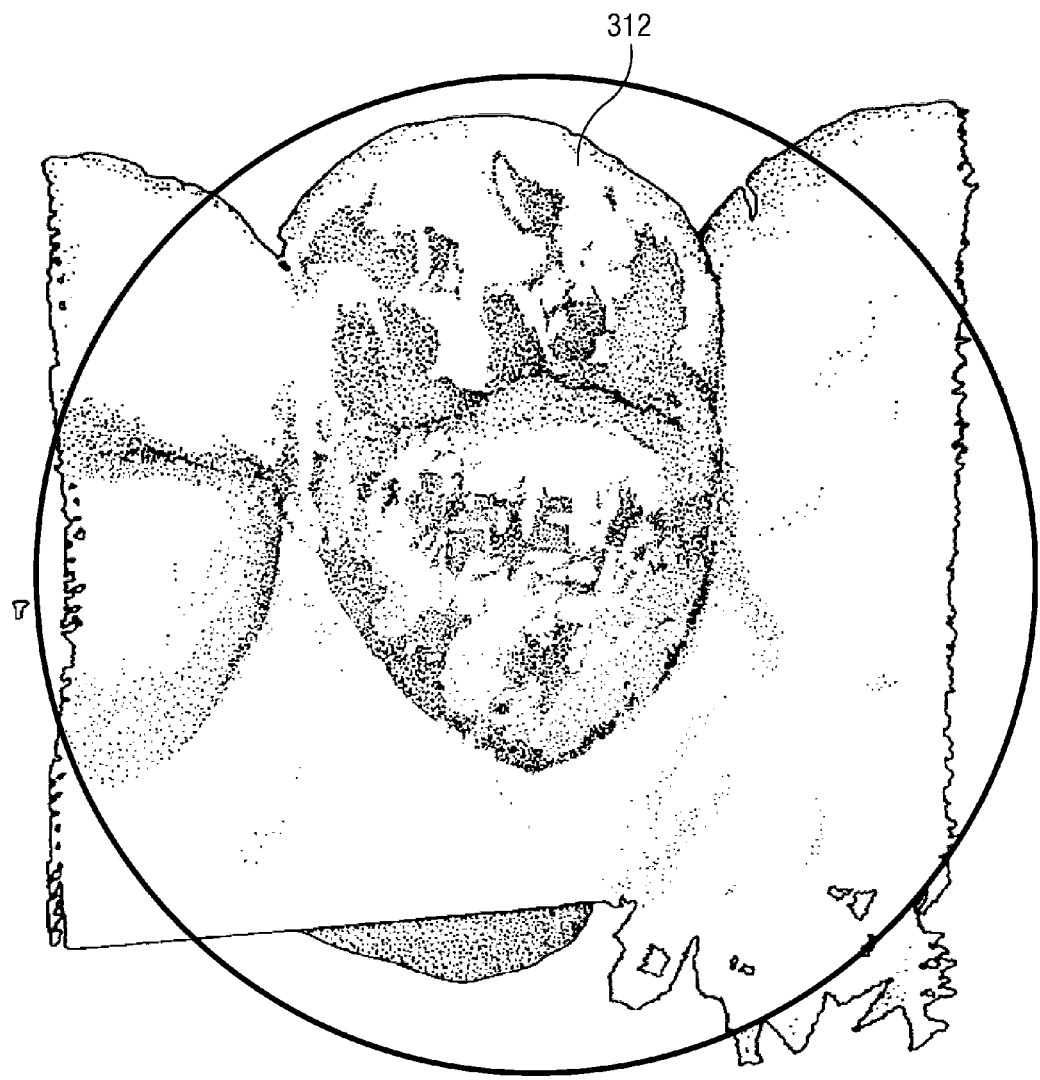
FIG. 5 is an illustration of the tooth model of FIG. 4D positioned in the computer model of the patient's dentition, surrounded by other anatomical structures.

The final result, an individual three-dimensional virtual tooth object 312, is then displayed to the user, as shown in FIG. 5. The result may be displayed on the workstation user interface as a three-dimensional superposition of the original data (white) and the separated model of the tooth (darker tones or contrasting color). These tones allow the user to ascertain whether there is an even distribution of white and dark tones, indicating good fit between the scanned tooth 308 and the individual tooth object 312. This step may be automated by an algorithm detecting the difference (or the sum of the differences), and repeating the process if the difference is too great.

Separation of teeth from the virtual model of the dentition could also be performed automatically using algorithms to detect incisal edges of the teeth, grooves between teeth, and grooves indicating the intersection of the gums and the teeth. Two types of errors can occur when separation of teeth objects from other structure (e.g., other teeth and gums): 1) the data is selected for a tooth that does not in actuality belong to the tooth, such as gums and adjacent teeth, and 2) data that does belong to the tooth is ignored. The entire process including these and other aspects is described in greater detail in the patent application of Rüdger Rubbert, et al., filed Apr. 13, 2001, entitled METHOD AND WORKSTATION FOR GENERATING VIRTUAL TOOTH MODELS FROM THREE-DIMENSIONAL TOOTH DATA, Ser. No. 09/834,413, pending, the entire contents of which are incorporated by reference herein.

This process is of course performed for all the teeth. The result is a set of individual tooth objects for all the teeth in the patient's dentition. The teeth can be displayed either alone, or in conjunction with the surrounding anatomical structures such as shown in FIG. 5.

Figure 6:
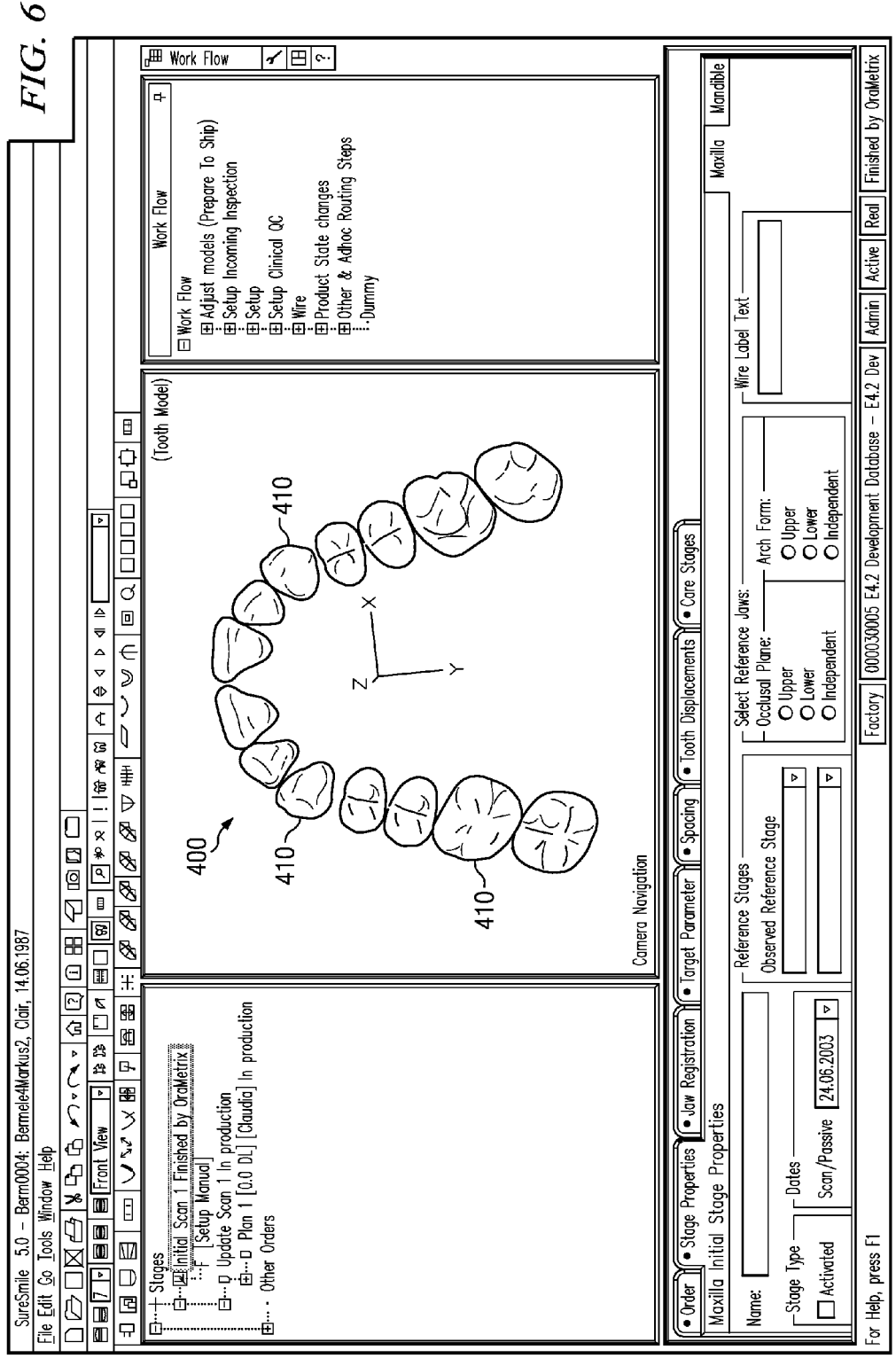
FIG. 6 is a screen shot displaying a buccal view of the individual tooth objects created from the maxilla jaw of a patient using the tooth separation process.

FIG. 6 is a screen shot displaying a buccal view 400 of the individual tooth objects 410 created from the maxilla jaw of a patient using the tooth separation process described above.

The tooth model, once created, can be modified to simulate various treatments that may be made on the tooth.

Treatment Planning

The virtual model of the patient's dentition, and the individual tooth objects created as explained above, provide a base for diagnostic analysis of the dentition and treatment planning Treatment planning software is provided on the workstation of the orthodontic clinic, and possibly at other remote locations such as the precision appliance center of FIG. 1. The treatment planning software can be considered an interactive, computer-based computer aided design and computer aided manufacturing (CAD/CAM) system for orthodontics. The apparatus is highly interactive, in that it provides the orthodontist with the opportunity to both observe and analyze the current stage of the patient's condition, and to develop and specify a target or desired stage. A shortest direct path of tooth movement to the target stage can also be determined. Further, the apparatus provides for simulation of tooth movement between current and target stages. For further details on treatment planning, refer to the previously mentioned patent application of Rüdger Rubbert et al., filed Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, now issued as U.S. Pat. No. 6,648,640, the entire contents of which are incorporated by reference herein.

Tooth features, such as the cusp tips, marginal ridges, central groove lines, buccal grooves, contact points, etc. play key roles in defining some well established orthodontic treatment planning criteria such as: alignment, marginal ridges, buccolingual inclination, occlusal relationships, occlusal contacts, interproximal contacts, root angulation, etc. Indeed, the American Board of Orthodontics (ABO) has introduced an Objective Grading System (OGS) for evaluating the results of an orthodontic treatment once it is completed using these criteria.

Tooth Features

Methods for digitally finding the tooth features, such as the tooth axes system, marginal ridges, cusp tips, contact points, central groove lines, and buccal grooves on a virtual three-dimensional model of a tooth, according to preferred embodiments of the invention, will now be described.

Tooth Axes System

Figure 7A:
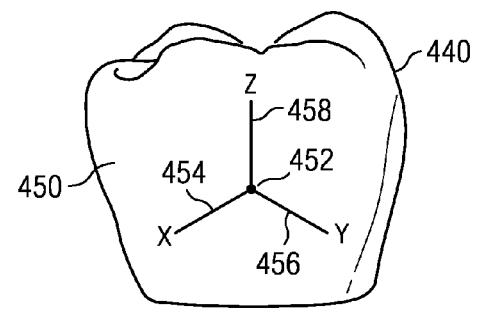
FIG. 7A shows the tooth axes system for a virtual tooth as an example.

FIG. 7A shows the tooth axes system (TAS) 450 for the virtual tooth 440 as an example. TAS 450 comprises the origin 452, the x-axis 454 in the mesial and distal directions, the y-axis 456 in the buccal and lingual directions and the z-axis 458 in the occlusal and gingival (vertical) directions. TAS is created for each individual tooth based up on the ideal properties of the tooth in terms of its features; and is not derived from the jaw features. TAS is preferably an anatomical coordinate system for the tooth. It is preferably derived during virtual modelling of the tooth from the scanning data and the tooth templates, and is adjusted if necessary.

Figure 7B:
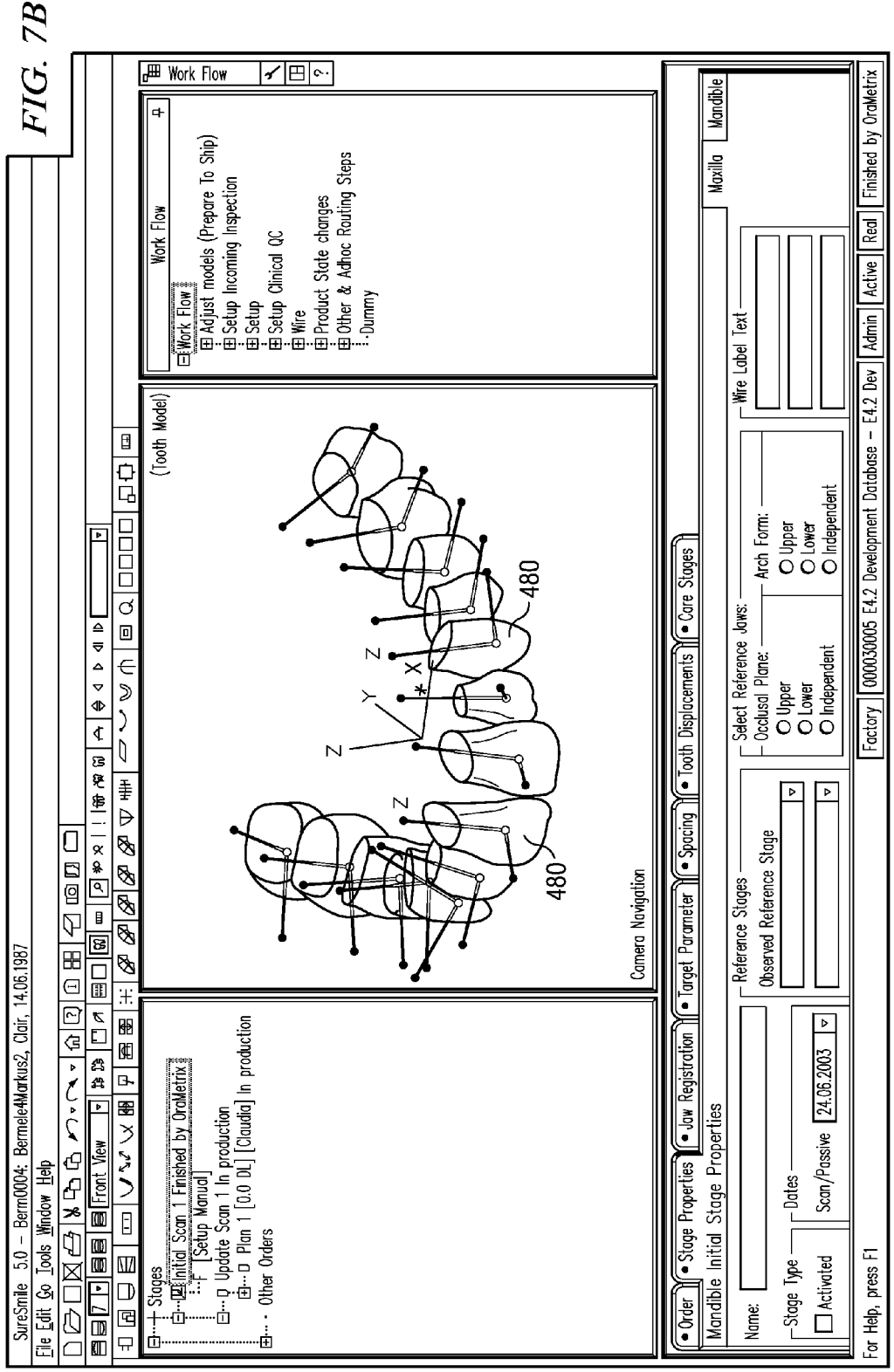
FIG. 7B shows an example of the tooth axes system for each tooth in the maxilla of a patient.

FIG. 7B shows an example of the TAS 480 for each tooth in the maxilla of a patient. The y-axis and the z-axis of each TAS are shown in FIG. 7B; however the x-axis is not shown for simplicity sake. TAS for a tooth behaves independently of the TAS for other teeth. Orientation of TAS is as such not fixed in space. Indeed TAS for any tooth moves with the tooth, and its position is determined by the position of the tooth. TAS plays an important role in tooth position measurements.

Rotation Matrix

A 3×3 rotation matrix $M^{rot}(v,\alpha)$ is defined so that for $x \in R^3$ $M^{rot}(v,\alpha) \cdot x$ is x rotated around the axis v by the angle $\alpha$ per Eq. (1);

where, v must have length 1 (one), i.e. $\sqrt{v_x^2+v_y^2+v_z^2}=1$.

$$M^{rot}(v, \alpha) := \begin{pmatrix} (1-\cos\alpha) \cdot v_x \cdot v_x + \cos\alpha & (1-\cos\alpha) \cdot v_x \cdot v_y - v_z \cdot \sin\alpha & (1-\cos\alpha) \cdot v_x \cdot v_z + v_y \cdot \sin\alpha \\ (1-\cos\alpha) \cdot v_y \cdot v_x + v_z \cdot \sin\alpha & (1-\cos\alpha) \cdot v_y \cdot v_y + \cos\alpha & (1-\cos\alpha) \cdot v_y \cdot v_z - v_x \cdot \sin\alpha \\ (1-\cos\alpha) \cdot v_z \cdot v_x - v_y \cdot \sin\alpha & (1-\cos\alpha) \cdot v_z \cdot v_y + v_x \cdot \sin\alpha & (1-\cos\alpha) \cdot v_z \cdot v_z + \cos\alpha \end{pmatrix} \quad \text{Eq. (1)}$$

The procedures for finding several tooth features require tooth rotations at desired angles. The tooth rotation is accomplished by using Eq. (1).

Ridge for Molars and Pre-Molars

The process of finding some of the tooth features, according to a preferred embodiment of the invention, starts with finding the ridge on the occlusal side of the tooth model surface for molars and premolars.

Figure 8:
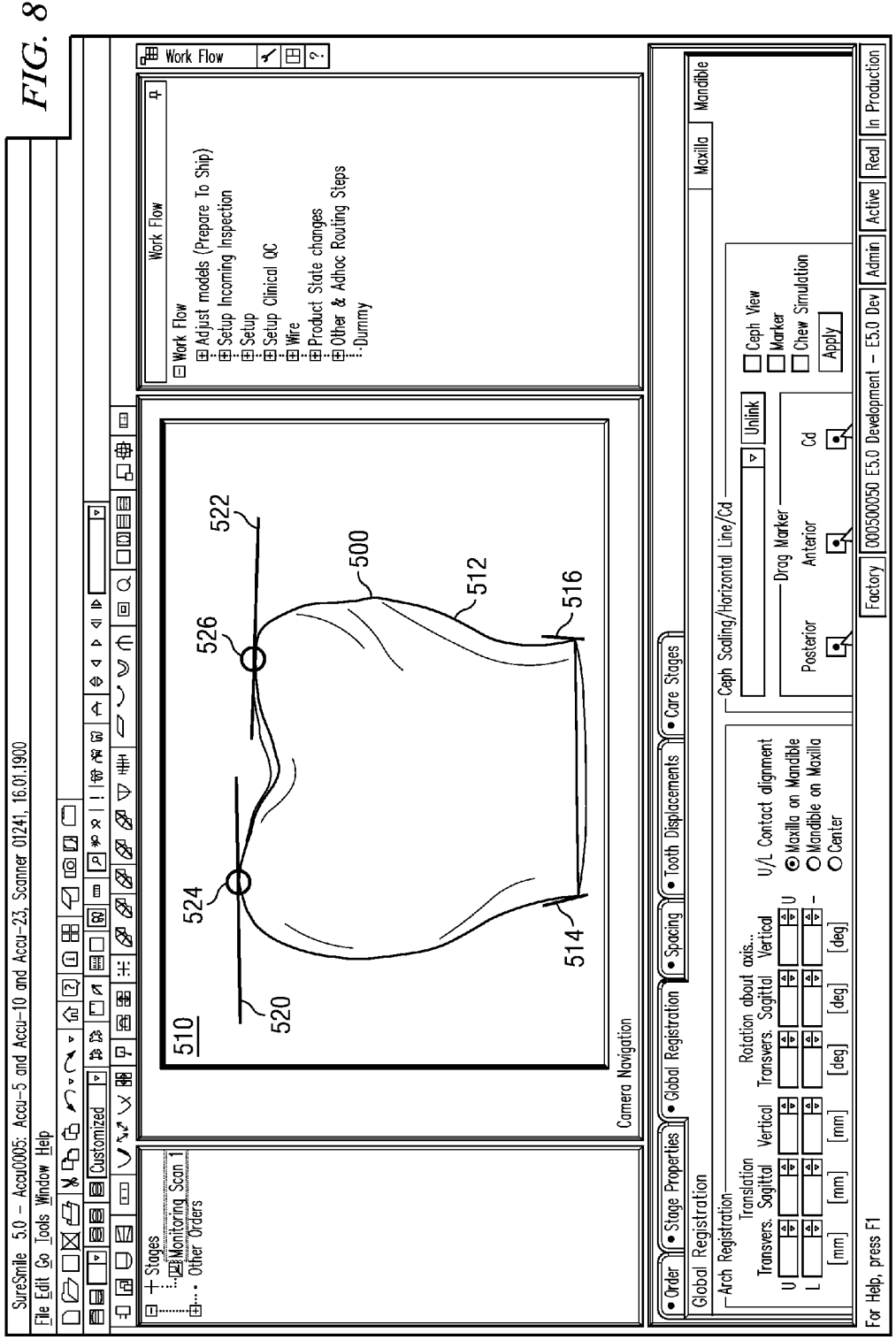
FIG. 8 shows a screen shot illustrating the process for finding the ridge on a virtual tooth surface, according to a preferred embodiment of the invention.
Figure 9:
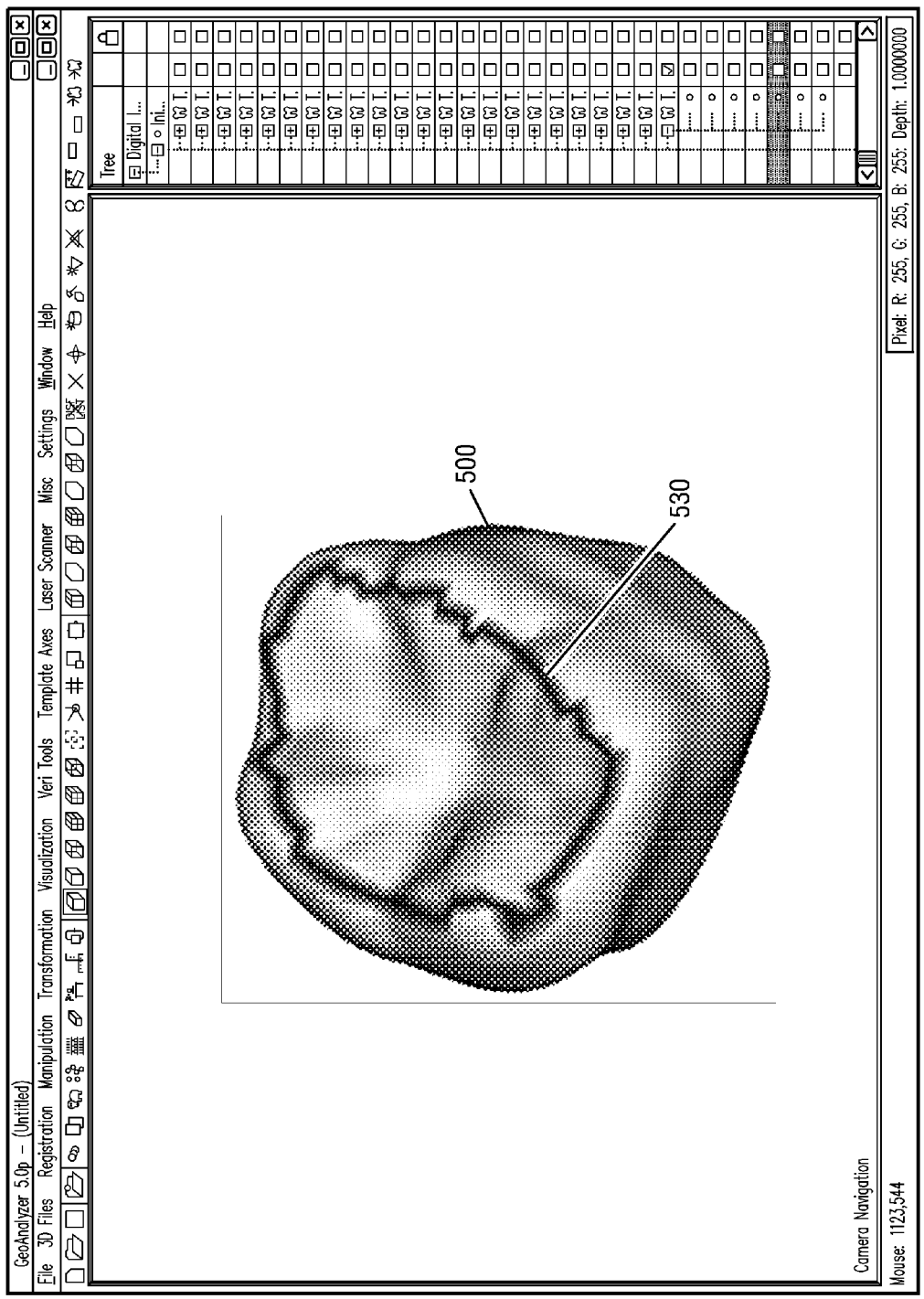
FIG. 9 shows a screen shot illustrating the ridge on a virtual tooth model surface, according to a preferred embodiment of the invention.

FIG. 8 shows a screen shot illustrating the process for finding the ridge on a tooth surface. First, a plane 510 is defined containing the z-axis from the TAS of the virtual tooth 500 under consideration such that the plane intersects the entire surface of the tooth model and forms a curve 512 along the surface of the tooth model. Next, the curve 512 is traced starting from the bottom of the tooth (the face opposite to the occlusal surface) first on one side (e.g. left) with the help of a moving tangent 514 and then the other side (e.g. right) with the help of a moving tangent 516 applied to the curve. When the tangent 514 becomes horizontal as the tangent 520 (i.e., having the vanishing z-coordinate) it designates the ridge point 524 on the curve and consequently on the surface of the tooth; and the tracing process with respect to this curve is stopped in this direction. Alternately, the curve tracing process may be stopped when the tangent becomes close to horizontal as defined by an arbitrary threshold, for example 5 degrees. The tangent 516 in the other direction leads to the horizontal tangent 522 and the ridge point 526. Two ridge points 524 and 526 on the surface of the tooth are thus found by tracing the curve. These two ridge points 524 and 526 with respect to the plane 510 are recorded. The plane is then rotated by a certain angle (for example 15 degrees) using Eq. (1), while still containing the z-axis of the tooth, and it intersects the tooth surface producing another curve along the surface of the tooth model. The process of tracing the curve is repeated and another set of two ridge points on the surface of the tooth are found. The process of rotating the plane and tracing the curve is repeated until the entire surface of the tooth model has been explored. For each position of the plane a set of two ridge points on the surface of the tooth model are found. The two ridge points in any set will (normally) be on opposite sides of the z-axis. As illustrated by FIG. 9, this family of the ridge points defines the ridge 530 of the virtual tooth 500.

Marginal Ridges of Molars and Premolars

Figure 10:
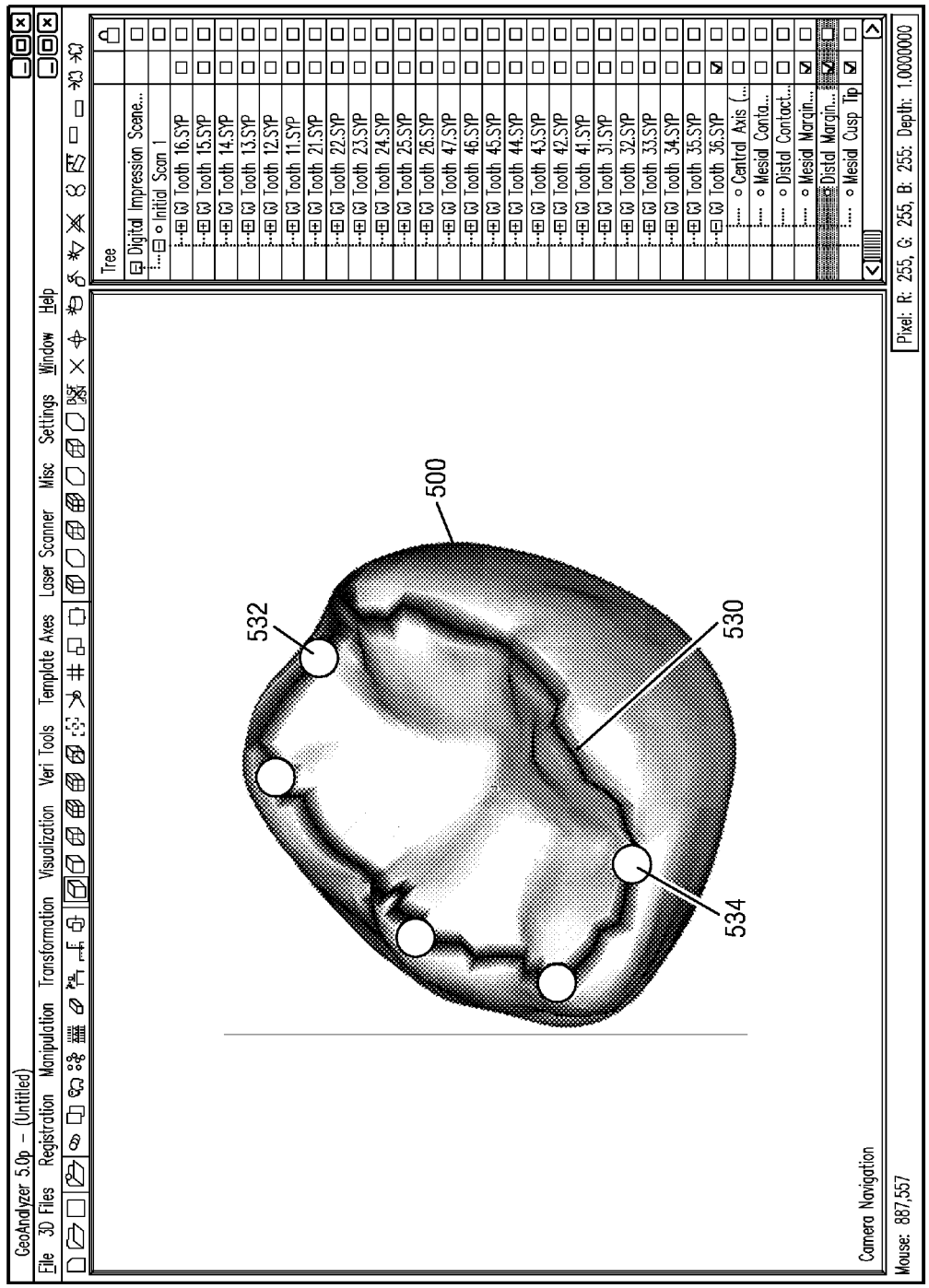
FIG. 10 illustrates a screen shot showing the marginal ridges on a virtual tooth, according to a preferred embodiment of the invention.

Marginal ridges are the tooth features for molars and premolars. According to a preferred embodiment of the invention, as illustrated in FIG. 10, two local minima 532 and 534, one at the mesial side of the tooth, and another at the distal side of the tooth are found from the ridge family of points 530 for the virtual tooth 500. These two minima 532 and 534 are the marginal ridges for the tooth.

Figure 11:
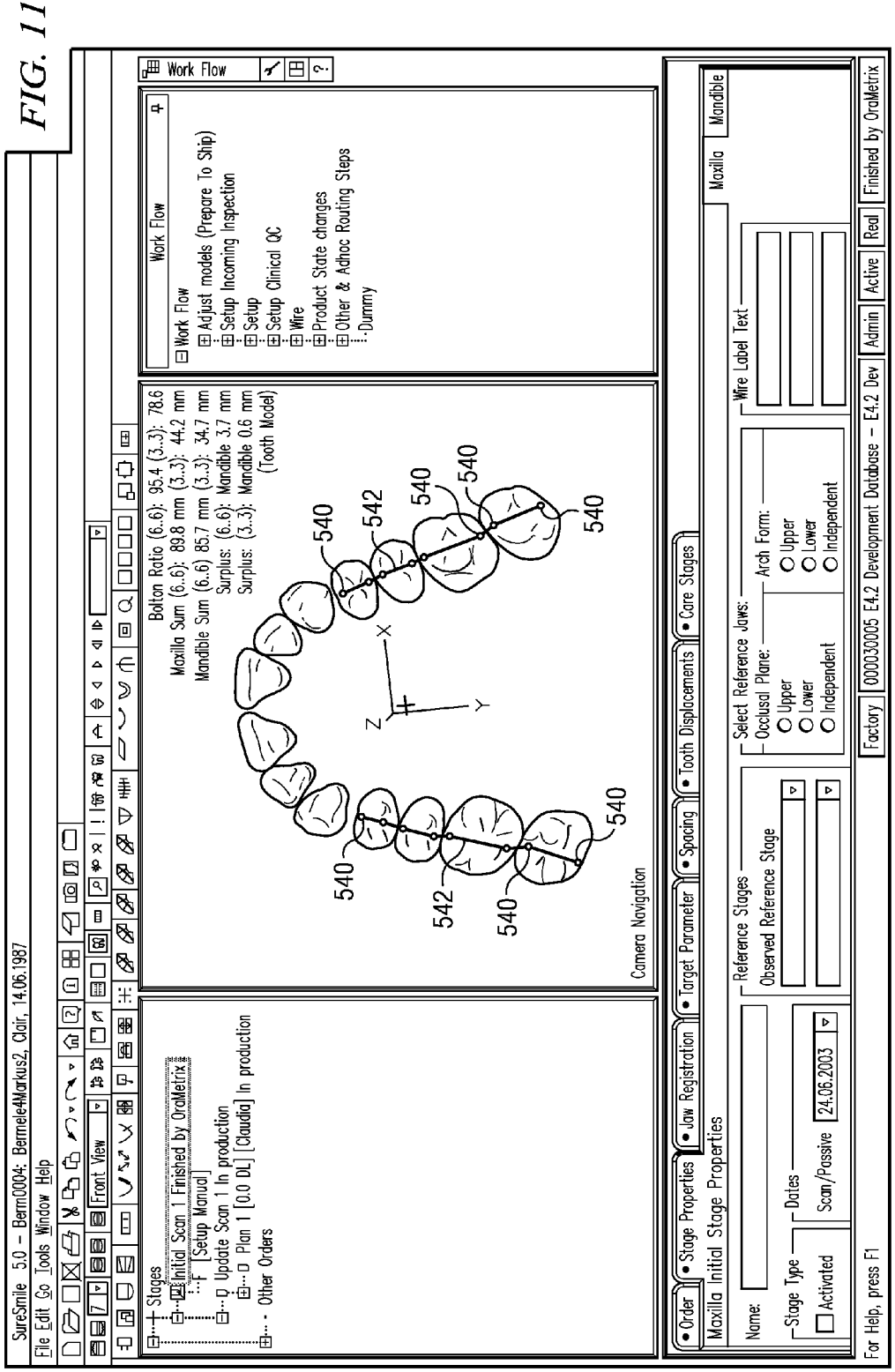
FIG. 11 illustrates a screen shot showing marginal ridges on a group of teeth, according to a preferred embodiment of the invention.
Figure 12:
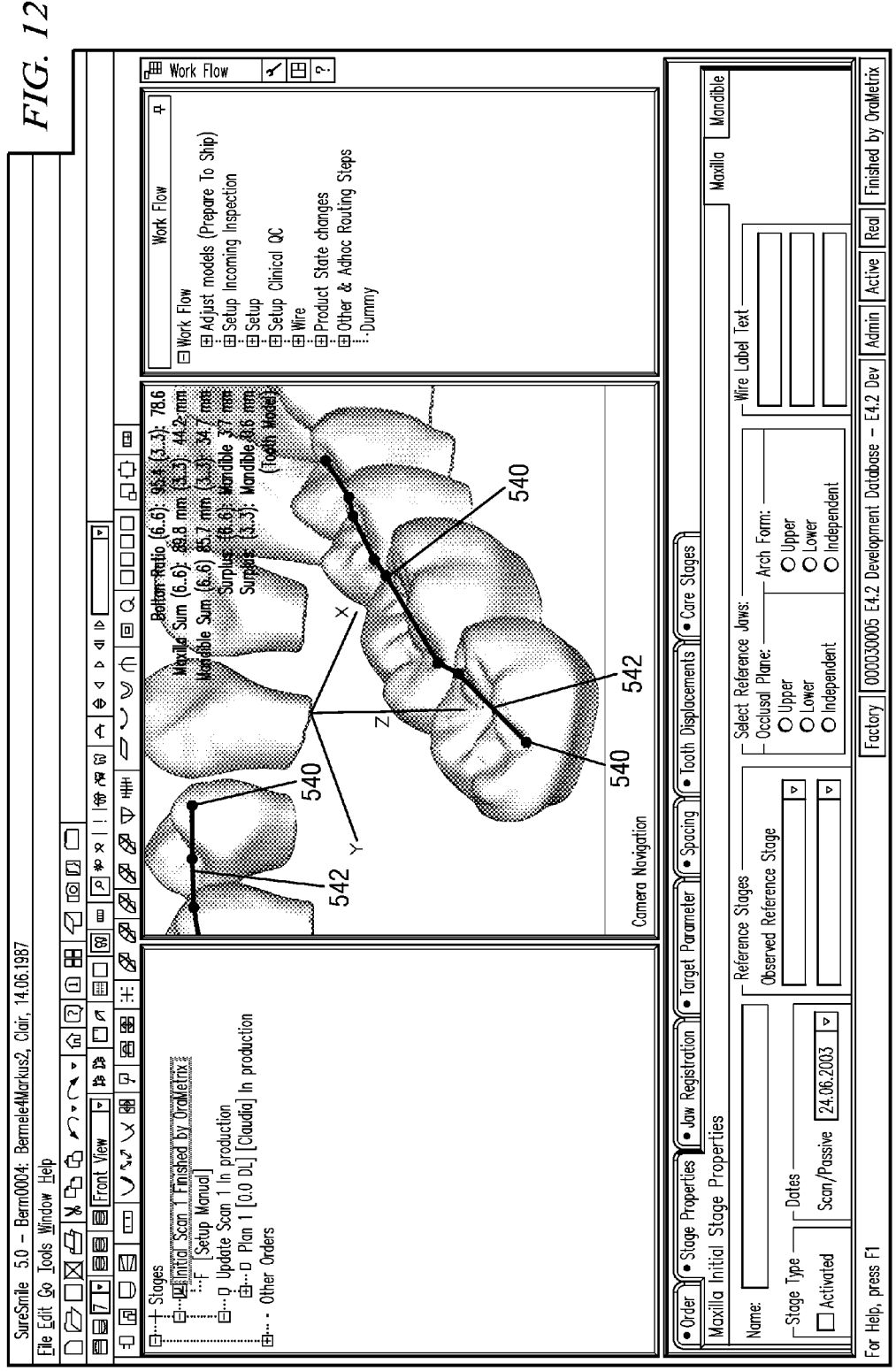
FIG. 12 illustrates another screen shot showing marginal ridges on a group of teeth, according to a preferred embodiment of the invention.

FIGS. 11 and 12 illustrate screen shots showing marginal ridges 540 on a group of teeth. Lines 542 connecting the marginal ridges are only shown for illustrative purposes.

There are different ways possible for defining these two minima. In one aspect, the tooth surface is divided into two halves, one with positive x-coordinates, and another with negative. In each of these halves the absolute minimum of the ridge is taken as a marginal ridge. In another aspect, the whole tooth model is rotated around its y-axis by 45 degrees, once in each of the two directions, each time searching the absolute minimum of the rotated ridge. One skilled in the art would appreciate that other approaches for determining the marginal ridges are possible as well.

Cusp Tips of Molars and Premolars

Figure 13:
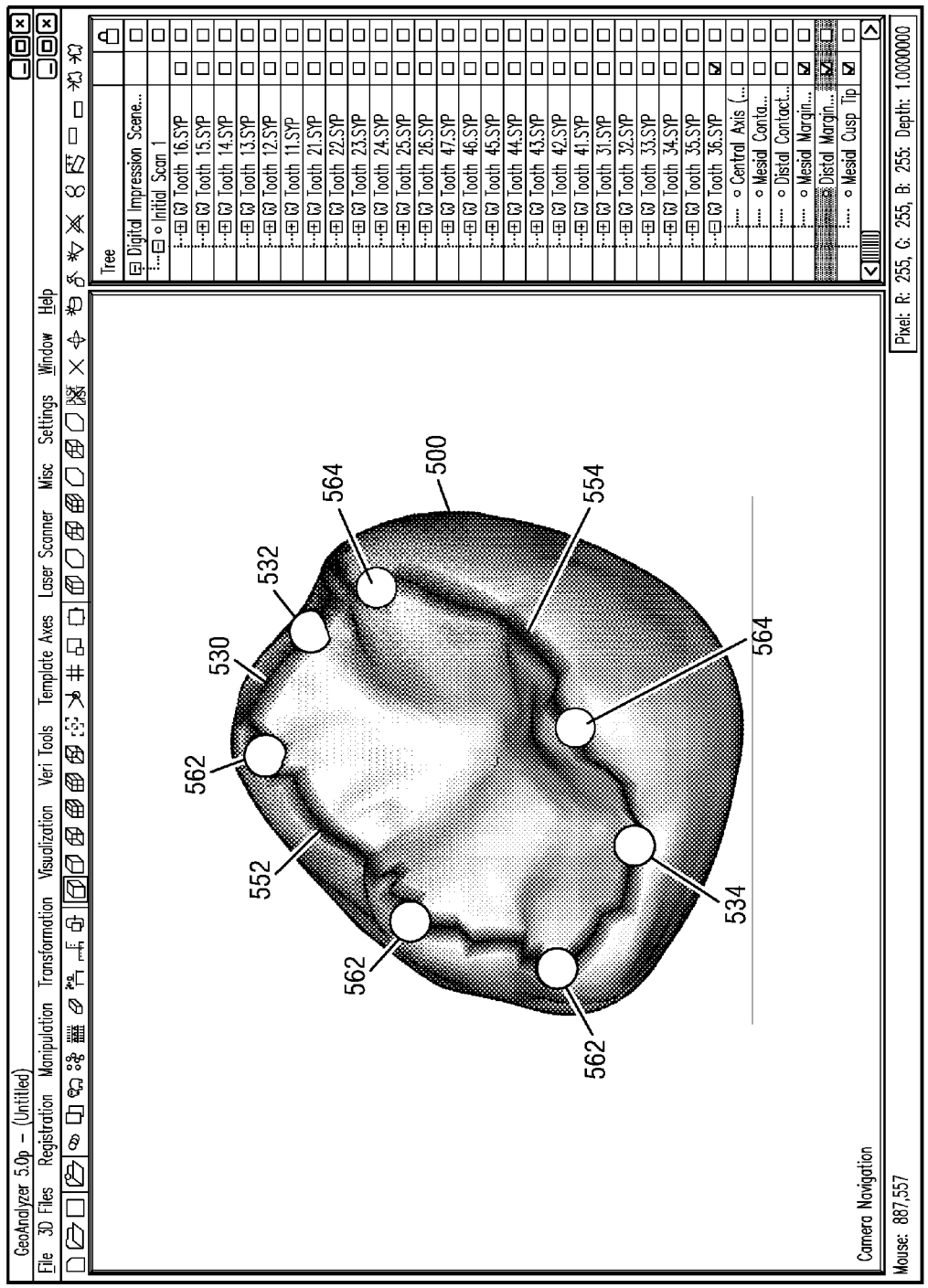
FIG. 13 shows a screen shot illustrating the marginal ridges and the cusp tips on the virtual model of a tooth, according to a preferred embodiment of the invention.

The procedure for digitally finding the cusp tips for molars and premolars is explained with reference to FIG. 13, according to a preferred embodiment of the invention. In order to determine the cusp tips for a virtual tooth model 500, the marginal ridges 532 and 534 are used to divide the ridge 530 into two subsets 552 and 554, with each subset bounded by the two marginal ridges, one subset 552 at the buccal side of the tooth (the buccal branch), and the other 554 at the lingual side (the lingual branch). Now the local maxima (maximal z-coordinate) of the buccal branch define the buccal cusp tips 562 and the local maxima of the lingual branch define the lingual cusp tips 564.

If there are more local maxima along a branch than expected (according to the tooth morphology), then the most distinct ones are chosen. One skilled in the art would appreciate that there are different possibilities for defining the 'distinctness'. One preferred method is to find the preceding and the succeeding local minimum for each local maximum, and measure their 'distance' (this distance can be defined as the Euclidian distance, or as the angle between the intersecting planes used in finding the ridge), on which these mimima are situated.

Correction of Tooth Coordinate System

The cusp tips can be used to correct the TAS for a tooth, according to a preferred embodiment of the invention, as follows:

a) If there are at least three cusp tips, then the TAS is rotated in such a way that all cusp tips have (approximately) the same z-coordinate. If there are three cusp tips, they will have exactly the same z-coordinate. On the other hand, if there are more than three cusp tips, then an approximate a solution is found which minimizes the differences of the z-coordinates.

b) If there are two cusp tips (such as in premolars), then the TAS is rotated around an axis, which passes through the origin of the TAS for the tooth and is perpendicular to the z-axis and to the vector connecting the two cusp tips, by an angle such that the z-coordinates of the two cusp tips are equal.

In one aspect, when the TAS is corrected in a manner described above, the ridge, the marginal ridges and the cusp tips are determined again in order to improve the accuracy of the tooth features. Subsequently, the TAS is also refined, and the entire process of refining the tooth features is repeated. The process may be stopped when (a) a limit is reached in the angle of rotation of the correction applied to the TAS, or (b) the maximum iteration count is reached. Alternately, a combination of the iteration stopping criteria (a) and (b) can also be used.

Cusp Tips of Canines

Figure 14:
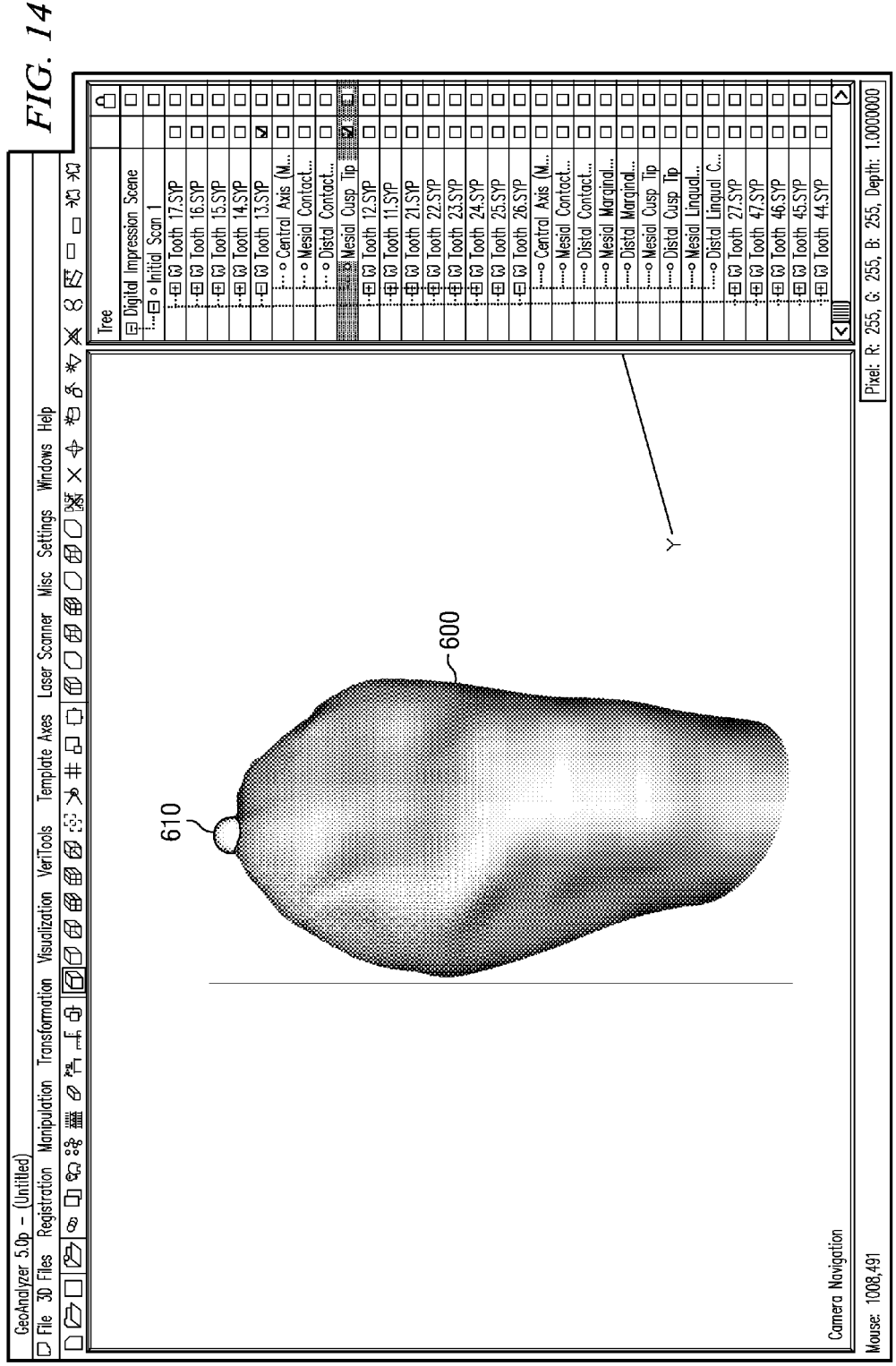
FIG. 14 shows a screen shot illustrating the single cusp tip of a canine tooth, according to a preferred embodiment of the invention.

Canines only have one cusp tip. The procedure for finding the cusp tip for a canine is illustrated with reference to FIG. 14, according to a preferred embodiment of the invention. The most or highest occlusal point 610 of the virtual tooth model 600 (the point with the highest z-coordinate) is chosen as the cusp tip for a canine tooth.

Cusp Tips of Front Teeth

For each front tooth, two points of the occlusal lateral edges are defined as the "cusp tips" for the purpose of an embodiment of the invention disclosed herein. With regard to these cusp tips, there is a differentiation made between maxilla and mandible front teeth. In the maxilla these two points are situated on the lingual side of the front teeth; while in the mandible they are situated on the labial side of the front teeth.

In order to determine these cusp tips, according to a preferred embodiment of the invention, the tooth model is rotated using Eq. (1) around the tooth TAS origin or any other point in the tooth, first by 45° in a) mesial direction, or b) distal direction; and after that in c) lingual direction, or d) labial direction. This whole procedure is repeated twice, once with direction a), then with direction b). This leads to the two points for the cusp tips. Direction d) is chosen for the maxilla teeth, direction c) for the mandible teeth.

After the rotation, the most or highest occlusal point of the rotated tooth model is chosen as a cusp tip.

One skilled in the art would appreciate that other approaches, instead of taking the most occlusal point at the cusp tip, are also possible finding the cusp tips for the front teeth. For example, in another embodiment of the invention, the centroid of the area comprising all points of the tooth model, which fulfills the condition that its z-coordinate differs not more than a certain threshold from the most occlusal point of the rotated tooth model, is chosen as the desired cusp tip.

Figure 15:
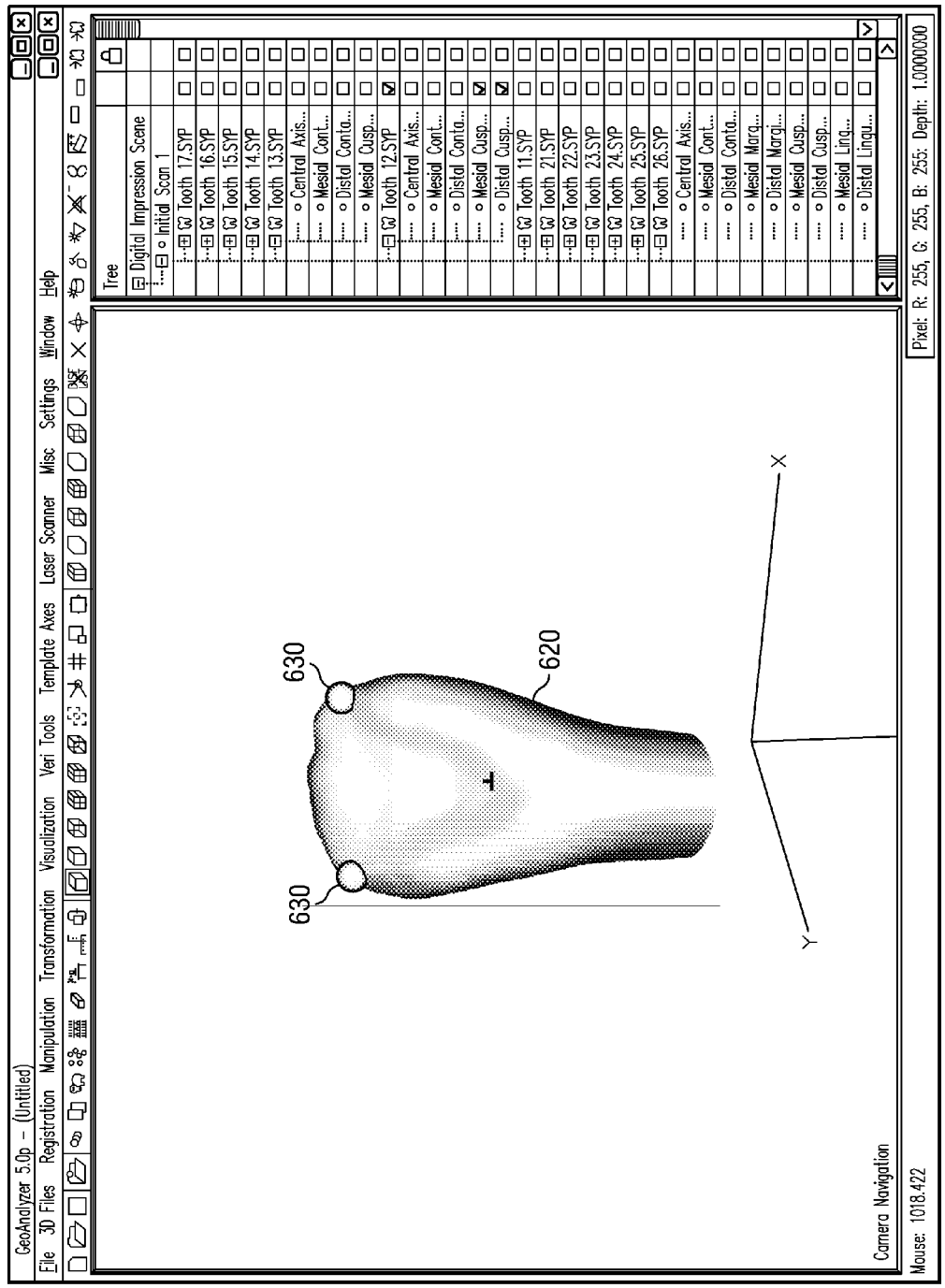
FIG. 15 shows a screen shot illustrating the two cusp tips of an upper front tooth, according to a preferred embodiment of the invention.

FIG. 15 shows a screen shot illustrating the two cusp tips 630 of an upper front tooth 620.

Figure 16:
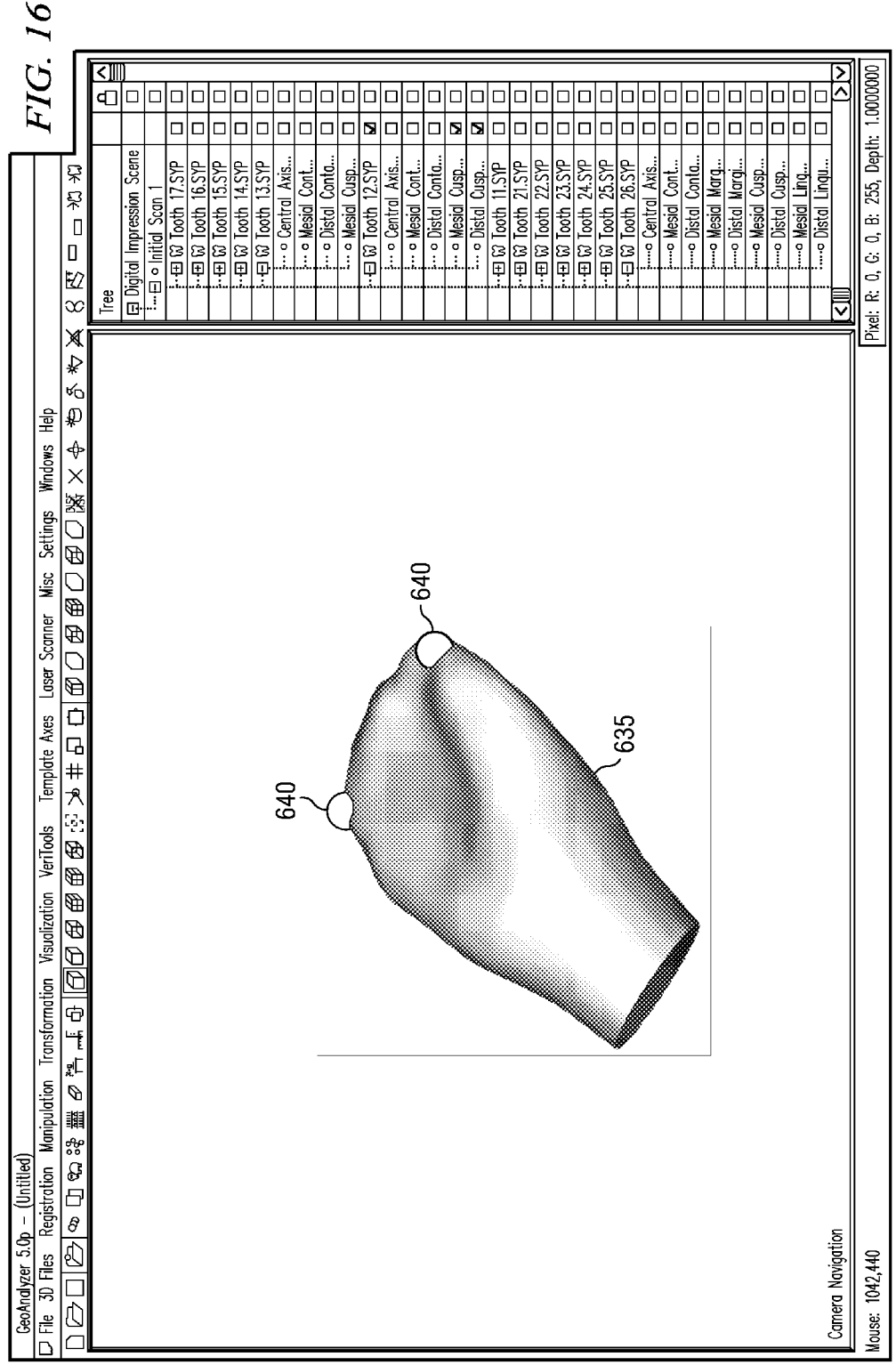
FIG. 16 shows another screen shot illustrating the two cusp tips of an upper front tooth, according to a preferred embodiment of the invention.

FIG. 16 shows another screen shot illustrating the two cusp tips 640 of an upper front tooth 635. In FIG. 16, the tooth was rotated by 45° to distal direction and 45° to labial direction. In this situation the left cusp tip was found as the most occlusal point.

Ideal Contact Points

In order to find the ideal contact points for a virtual tooth, according to a preferred embodiment of the invention, the surface of the tooth model is intersected with the x-y plane based up on the TAS for the tooth. Then, the most mesial point and the most distal point (i.e. points with the lowest/highest x-coordinates), are the two ideal contact points for the tooth.

Figure 17:
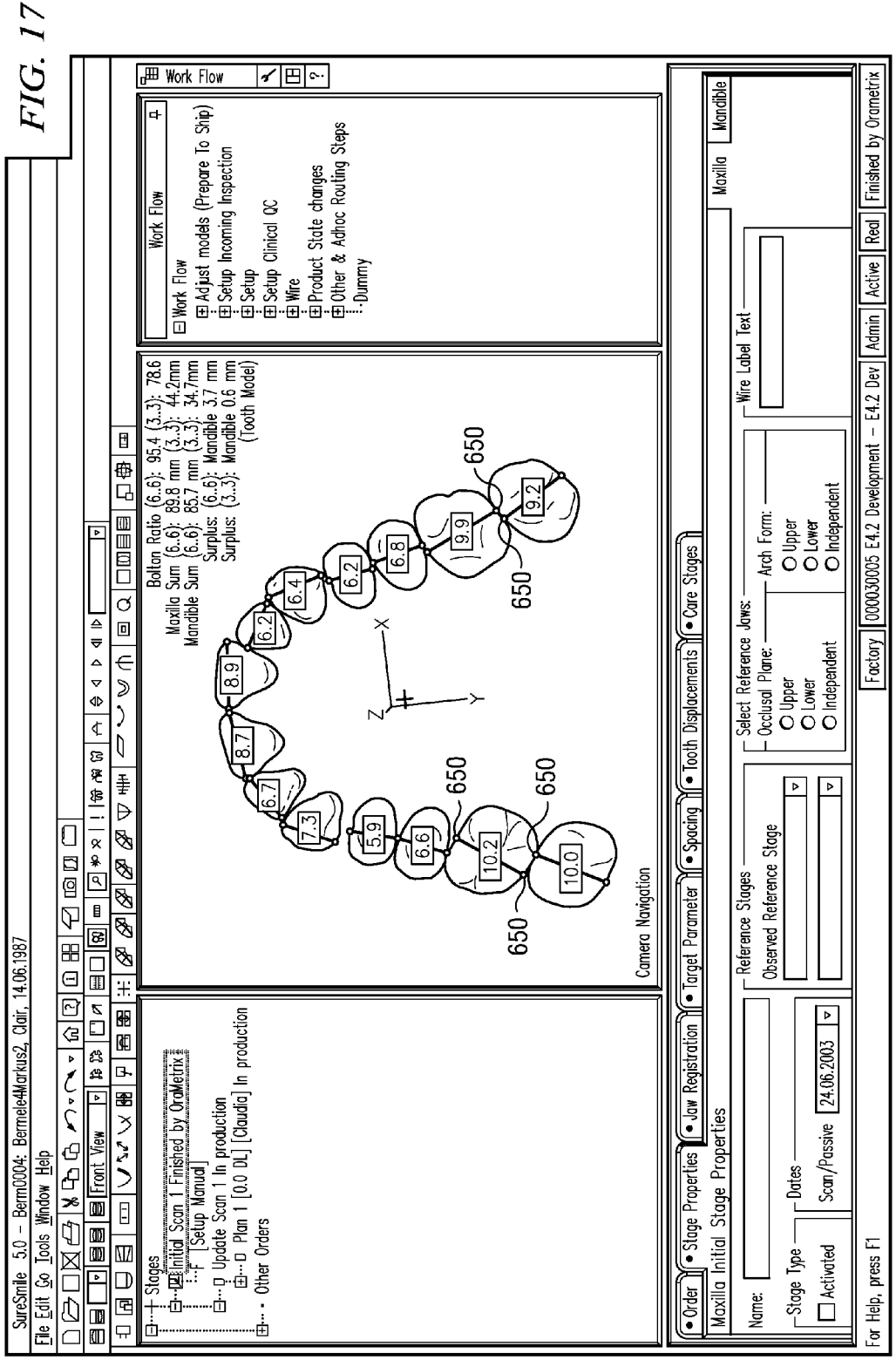
FIG. 17 shows a screen shot illustrating the ideal contact points on a patient's teeth in maxilla, according to a preferred embodiment of the invention.

FIG. 17 shows a screen shot illustrating the ideal contact points 650 on a patient's teeth in maxilla.

Central Groove

In order to determine the central groove for a tooth model, according to a preferred embodiment of the invention, the most occlusal (i.e. the point having the highest z-coordinate) cusp tips $C^l$ ($=(C^l_x, C^l_y, C^l_z)$) of the lingual side, and $C^b$ ($=(C^b_x, C^b_y, C^b_z)$) of the buccal side are determined using the procedure described earlier.

Figure 18:
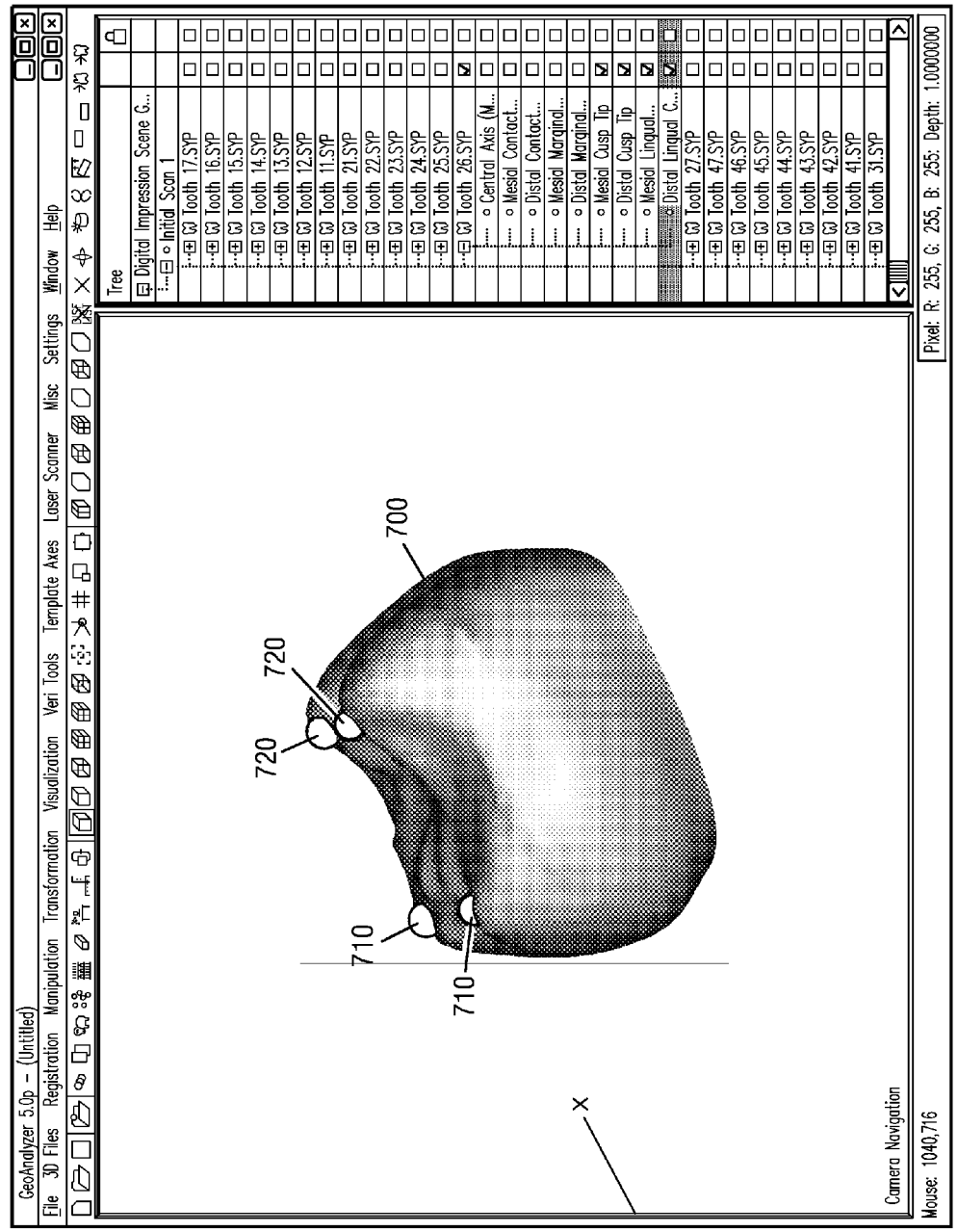
FIG. 18 shows a screen shot illustrating a tooth model presented in a distal view showing the lingual cusp tips and the buccal cusp tips, according to a preferred embodiment of the invention. The cusp tips are exaggerated in FIG. 18 for the purpose of better illustration.

FIG. 18 shows a screen shot illustrating a tooth model 700 presented in a distal view showing the lingual cusp tips 710 and the buccal cusp tips 720. The cusp tips are exaggerated in FIG. 18 for the purpose of better illustration.

Then, the tooth is rotated around the x-axis using the rotation matrix defined in Eq. (1), so that $C^l$ and $C^b$ have the same z-coordinates. This operation in effect means that the following transformation is applied.

$$V \mapsto v' := M^{rot}\left(\begin{pmatrix} 1 \\ 0 \\ 0 \end{pmatrix}, \alpha\right) \cdot v$$

with $$\alpha := \tan^{-1}\left(\frac{C^l_z - C^b_z}{C^l_y - C^b_y}\right).$$

Figure 19:
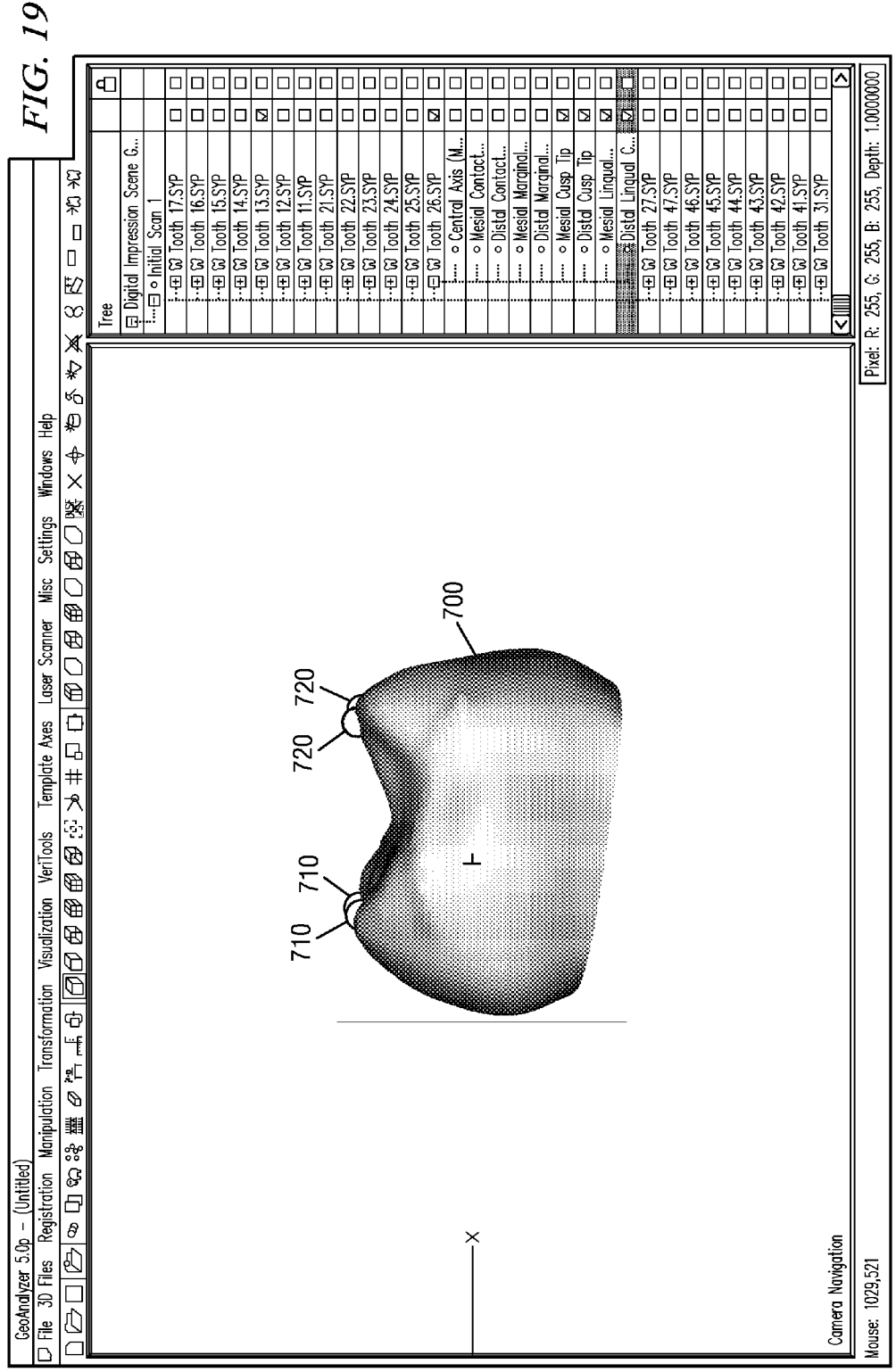
FIG. 19 shows a screen shot illustrating the virtual tooth model from a distal view, as shown in FIG. 18, after the rotation, according to a preferred embodiment of the invention. In this figure, the buccal cusp tips and the lingual cusp tips of the tooth have the same z-coordinate (i.e. the coordinate in the occlusal direction).

FIG. 19 shows a screen shot illustrating the virtual tooth model 700 from a distal view, shown in FIG. 18, after the rotation. In this figure, the buccal cusp tips 720 and the lingual cusp tips 710 of the tooth have the same z-coordinate (i.e. the coordinate in the occlusal direction). Again the cusp tips 710 and 720 are exaggerated for illustration purposes.

Next, a plane $E_k$ parallel to the y-z-plane is moved and cut with all edges of the tooth surface which is represented in the form of triangles derived during the registration process of the scanned tooth model, of which both vertex-normals point upwards. Then, the intersection points are sorted along the y-axis.

Figure 20:
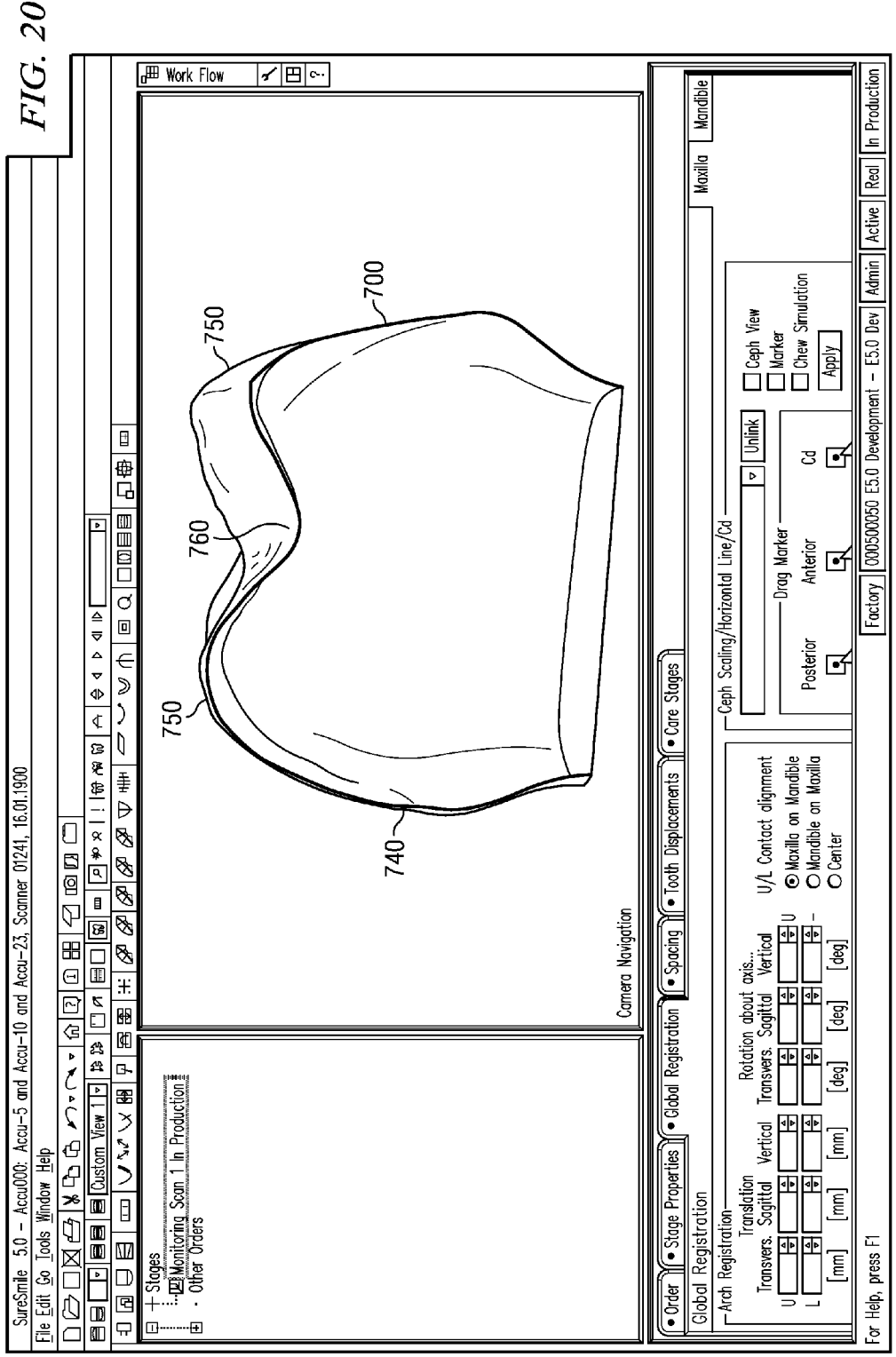
FIG. 20 shows a screen shot illustrating one intersection (or one slice) of the virtual tooth model shown in FIG. 19, according to a preferred embodiment of the invention. The tooth surface contour shows the typical shape of a molar with two "mountains" and a "valley" (the central groove).

FIG. 20 shows a screen shot illustrating one intersection (or one slice) of the virtual tooth model 700 shown in FIG. 19. The tooth surface contour 740 shows the typical shape of a molar with two "mountains" 750 and a "valley" 760 (the central groove). From each slice of the tooth surface, the deepest point of the valley is found using the following procedure.

Planes are selected as: $E_k$: $v_x = k \cdot d$ with $d=0.4$ (for example) and $k \in N$ The selection criterion is: A vertex normal n points upwards iff $n_z > 0.5$ (for example)

For each plane $E_k$ there is a series $(v^{k,i})_{i=1 \ldots I_k}$ with $v_y^{k,i} \leq v_y^{k,i+1} \forall i \in \{1, \ldots, I_k\}$, which are the intersection points of plane $E_k$ with the edges of the tooth-model. The criterion specified above assures that only the edges of the occlusal surface of the tooth are considered.

To each $v^{k,i}$ one then finds:

$m_<^{k,i} := \max\{v_z^{k,j}, j=1, \ldots i\}$, the maximum z-coordinate lingual of $v^{k,i}$, $m_>^{k,i} := \max\{v_z^{k,j}, j=i, \ldots I_k\}$, the maximum z-coordinate labial of $v^{k,i}$, $p^{k,i} := (m_<^{k,i} - v_z^{k,i}) \cdot (m_>^{k,i} - v_z^{k,i})$, the product of the differences between the z-coordinate of $v^{k,i}$ and the above two maxima.

Then, for each k an index $i_0^k$ is found so that $p^{k,i_0^k} = \max\{p^{k,i}, i=1, \ldots I_k\}$ is the maximum of these products.

Figure 21:
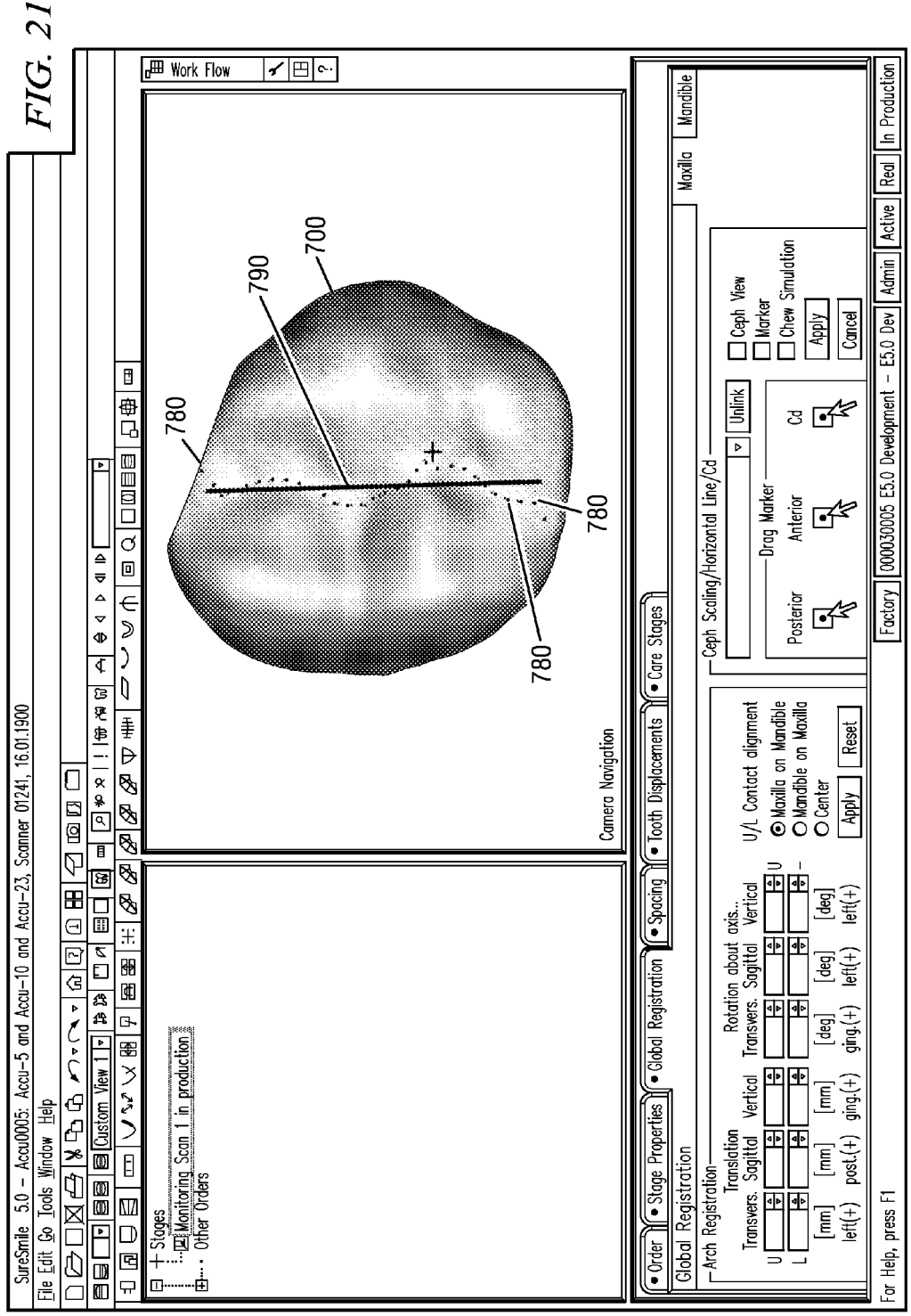
FIG. 21 shows a screen shot illustrating the points which are the deepest points, one of each slice, found in the process of determining the central groove, according to a preferred embodiment of the invention. The figure also shows the linear approximation of these points.
Figure 22:
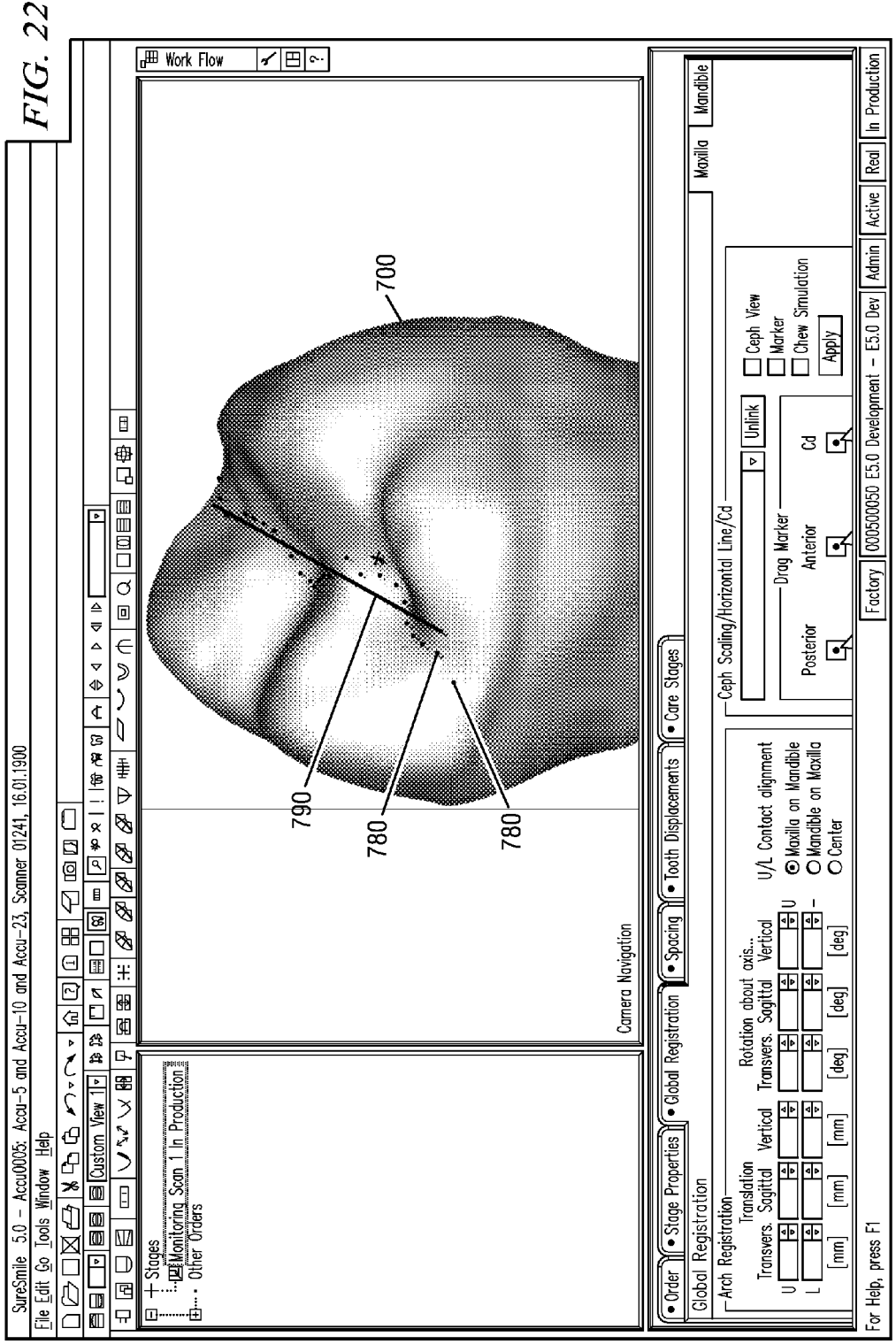
FIG. 22 shows a screen shot illustrating the tooth shown in FIG. 21 from another perspective, according to a preferred embodiment of the invention.

Next, referring to FIGS. 21 and 22, a linear approximation $l: x \mapsto (y,z)$ of the points 780 $(v^{k,i_0^k})_k$ is found, i.e. a (three-dimensional) line 790, which has minimal average (quadratic) distance to the points $v^{k,i_0^k}$. This line does not need to be the exact minimum, an approximation is good enough.

Using the two x-values
$x_{min} := \min\{v_x^{k,i_0^k}, \text{all } k\}$
$x_{max} := \max\{v_x^{k,i_0^k}, \text{all } k\}$
the following two points, $c_0$ and $c_1$ as defined below, are the end-points of the central groove 790 of the tooth 700.
$c_0 := (x_{min}, l(x_{min}))$
$c_1 := (x_{max}, l(x_{max}))$ FIG. 22 shows a screen shot illustrating the tooth 700 shown in FIG. 21 from another perspective.

Figure 23:
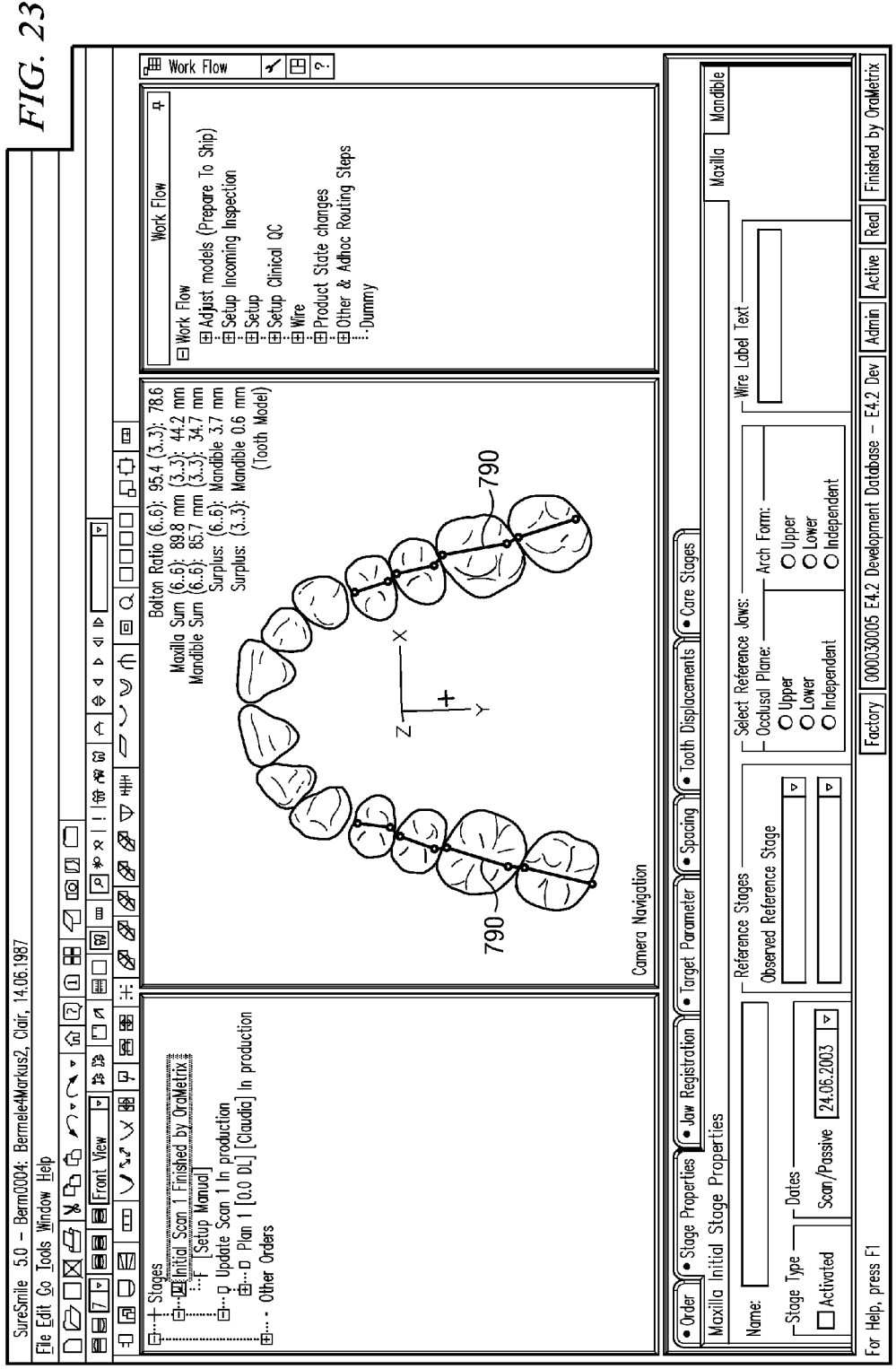
FIG. 23 shows a screen shot illustrating central grooves for several teeth models in the maxilla of a patient, according to a preferred embodiment of the invention.

FIG. 23 shows a screen shot illustrating central grooves 790 for several teeth models in the maxilla of a patient.

Figure 24:
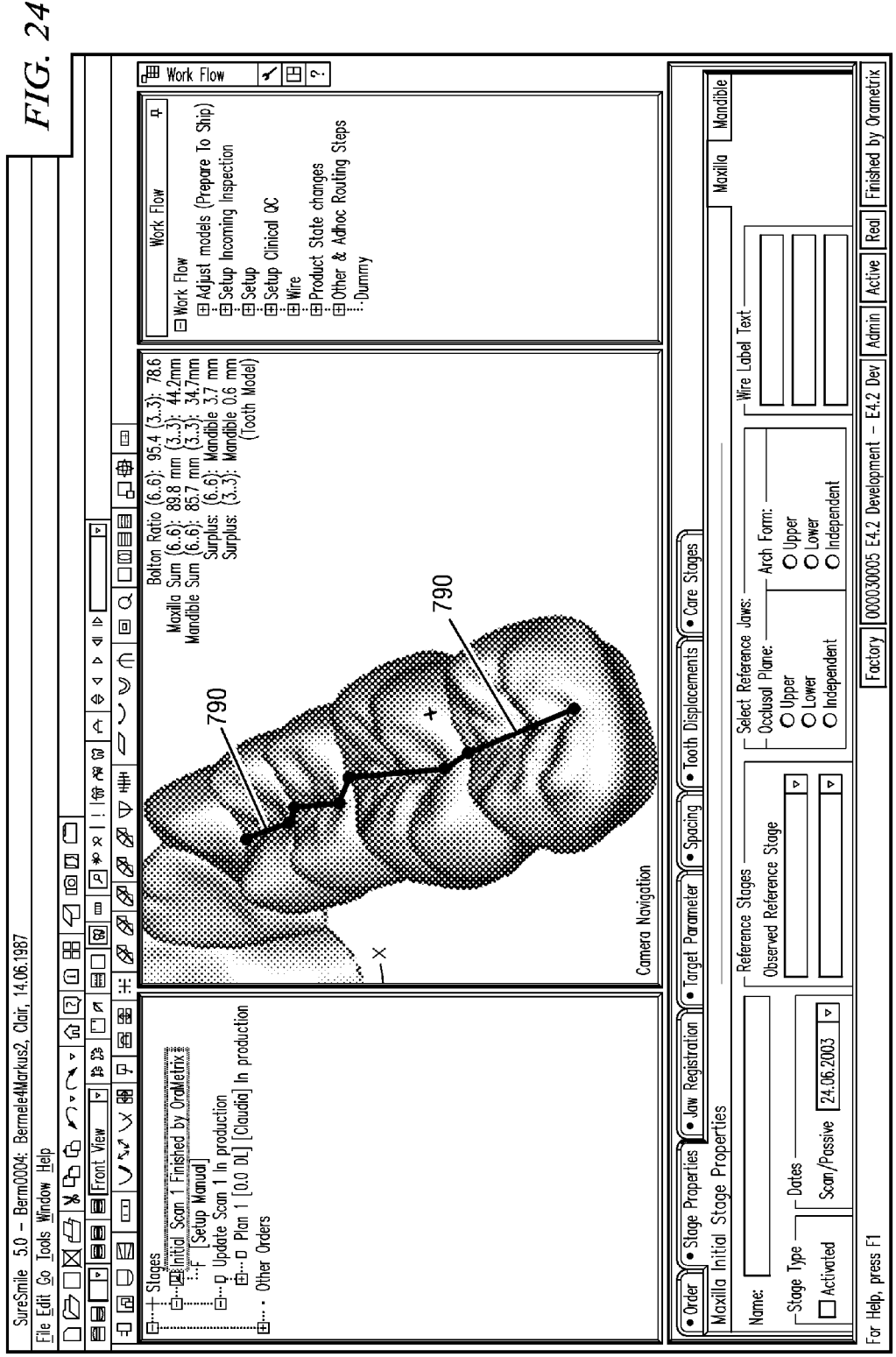
FIG. 24 shows another screen shot illustrating central grooves for several teeth models, according to a preferred embodiment of the invention.

FIG. 24 shows another screen shot illustrating central grooves 790 for several teeth models.

It should be noted that these central groove points $c_0$ and $c_1$ are in general not on the surface of the tooth model. Therefore, for proper use of the central groove in treatment planning, it is recommended to put the central groove points onto the tooth surface. One possibility for accomplishing this is to construct a line through $c_0$ and $c_1$, respectively, parallel to the z-axis of the TAS for the tooth (i.e. the occlusal direction), and cut it with all triangles of the tooth models. Of all intersection points, the most occlusal point (i.e. the point with the greatest z-coordinate) on the surface of the tooth is taken as the point representing the central groove. That is, the procedure is done once for $c_0$ and again for $c_1$.

Buccal Groove

The process of finding the buccal grove for a tooth model, according to a preferred embodiment of the invention, is described below.

Step 1. Let $\tilde{C}_M$ be the mesial labial cusp tip of the tooth-model of interest, and $\tilde{C}_D$ the distal labial cusp tip.

Then, find the two closest vertices $C_M$ and $C_D$, both $\in T = \{T_0, \ldots, T_N\} \subset R^3$ (T is the set of all vertices of the tooth-model, N is the number of vertices of the tooth-model):

$C_M := T_{i_M} \in T$ with $i_M \in \{1, \ldots, N\}$ so, that $\text{dist}(\tilde{C}_M, T_{i_M}) = \min\{\text{dist}(\tilde{C}_M, T_i), i \in \{1, \ldots, N\}\}$ $C_D := T_{i_D} \in T$ with $i_D \in \{1, \ldots, N\}$ so, that $\text{dist}(\tilde{C}_D, T_{i_D}) = \min\{\text{dist}(\tilde{C}_D, T_i), i \in \{1, \ldots, N\}\}$ (where $\text{dist}(P,Q) := \|P-Q\| := \sqrt{(P_x-Q_x)^2 + (P_y-Q_y)^2 + (P_z-Q_z)^2}$ is the Euclidean distance between two points.)

It should be noted that $i_M$ and $i_D$ are not always unique. If this is the case, simply one possible solution is chosen, for example the solution with the lowest index.

Figure 25:
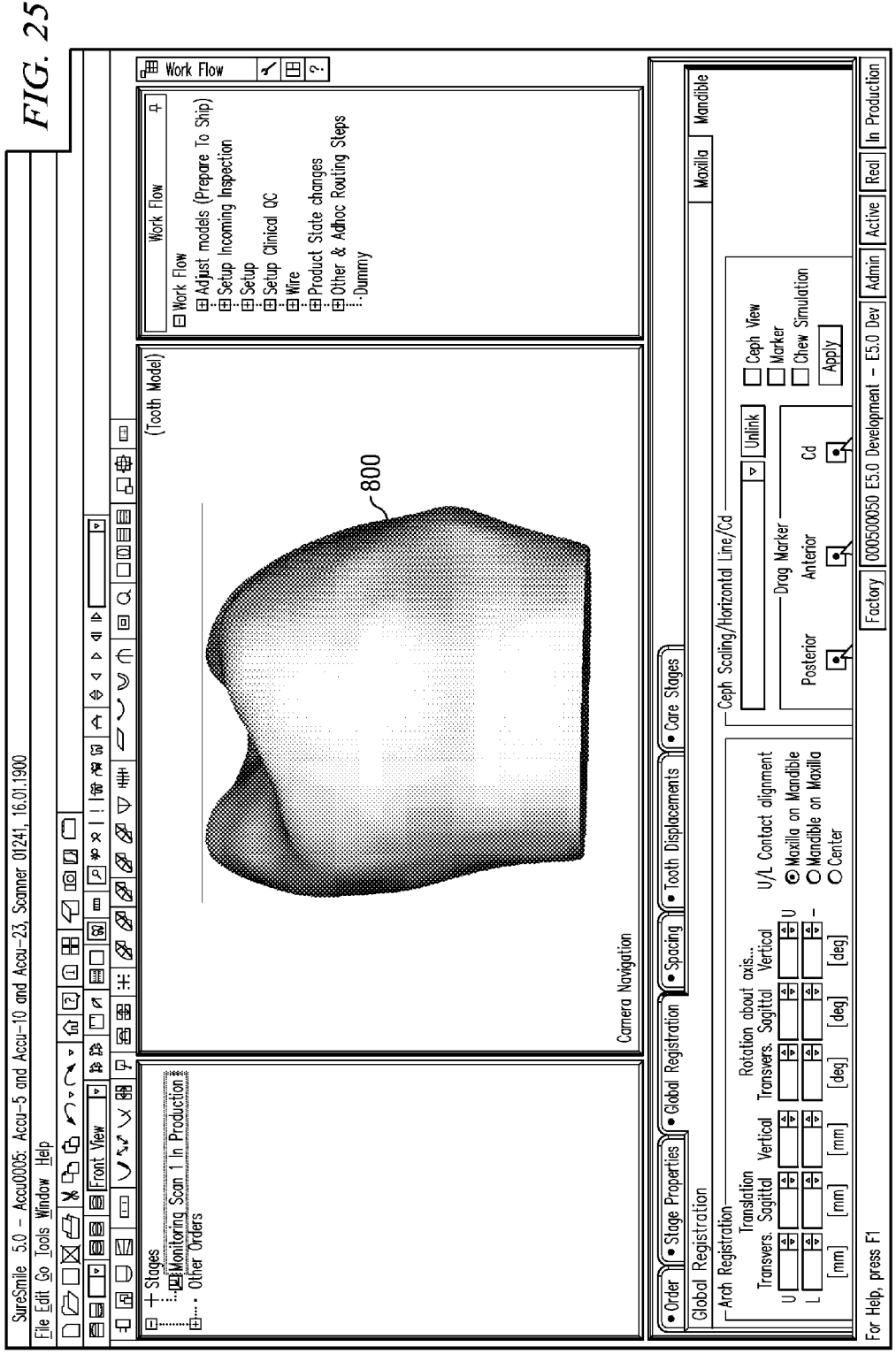
FIG. 25 shows a screen shot illustrating a tooth model from the distal view perspective in the process of determining the buccal grove, according to a preferred embodiment of the invention.

FIG. 25 shows a screen shot illustrating a tooth model 800 from the distal view perspective.

Step 2. Rotate the tooth-model around its x-axis (torque it) lingually by 60° using the following transformation matrix, using Eq. (1), $$M^T := M^{rot}\left(\begin{pmatrix}1\\0\\0\end{pmatrix}, 60\right)$$

Figure 26:
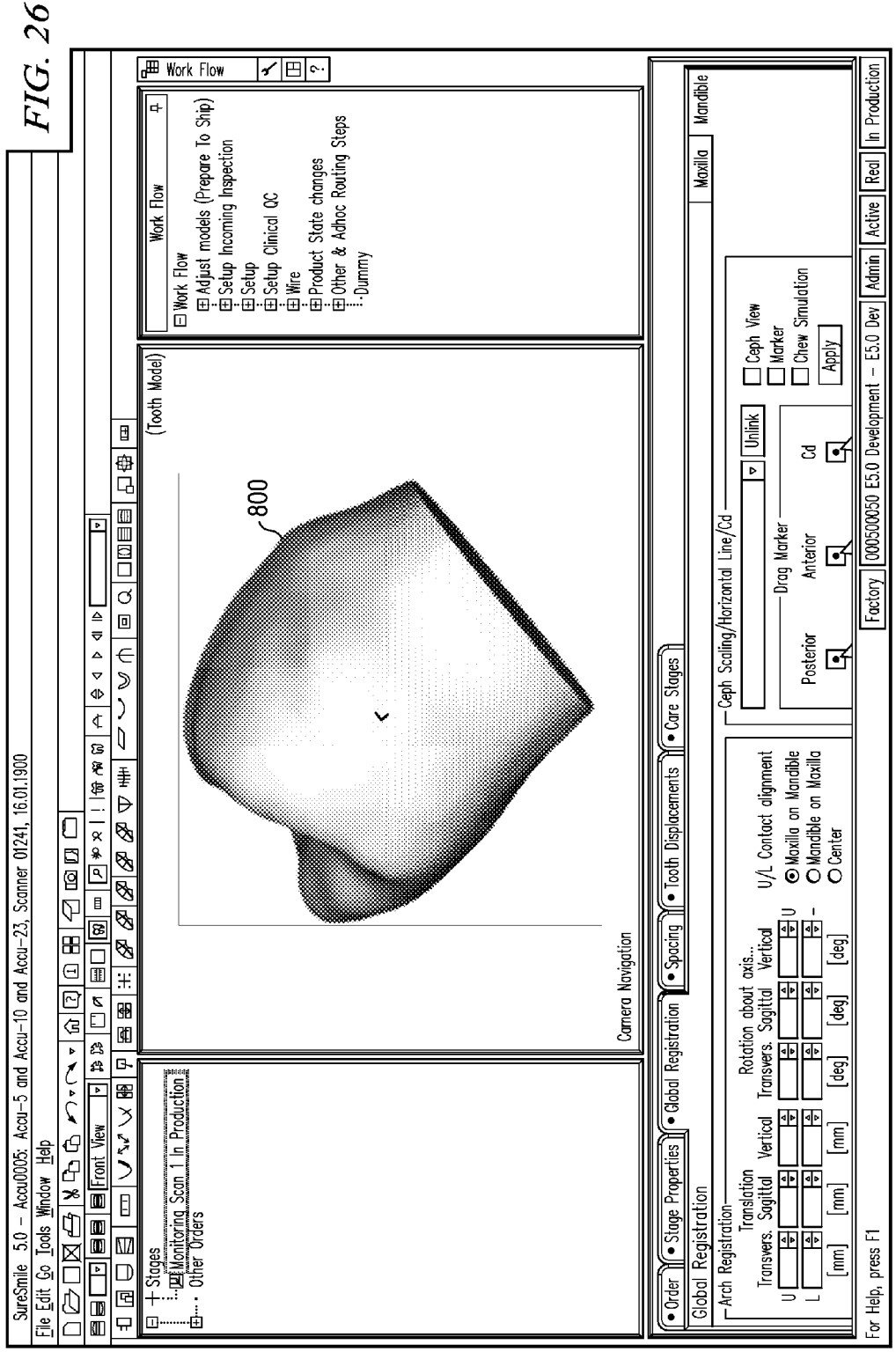
FIG. 26 shows a screen shot illustrating the tooth model, shown in FIG. 25, rotated 60 degrees to the labial side so that the labial side is nearly on top, according to a preferred embodiment of the invention.

FIG. 26 shows a screen shot illustrating the tooth model 800, shown in FIG. 25, rotated 60 degrees to the labial side so that the labial side is nearly on top.

Step 3. After this rotation, rotate the tooth-model around an axis, which is orthogonal to the z-axis and to the vector connecting the two cusps $C_M$ and $C_D$ so that the two cusps have the same z-coordinate (accomplished by performing the rotation R* described below).

Move the cusp tips along the tooth-surface, until they are on local maxima, and repeat rotation R* for each iteration of Step 3.

a) Perform rotation R*:
Axis:

$$v := \left(\begin{pmatrix}0\\0\\1\end{pmatrix} \times (C_D - C_M)\right)_0,$$

where $$w_0 := \frac{w}{\|w\|}$$

is the unit vector (vector with length 1).
Angle:

$$\alpha := \sin^{-1}\left(\frac{(M^T \cdot C_D)_z - (M^T \cdot C_M)_z}{\|C_D - C_M\|}\right)$$

Apply rotation to our transformation matrix $M^T$:
$M^T \leftarrow M^{rot}(v, \alpha) \cdot M^T$ b) Choose one of the two cusp tips, which has been moved less up to now (or any, if they have been moved equally). So, below, C will stand for $C_M$ if $\text{dist}(C_M, \tilde{C}_M) < \text{dist}(C_D, \tilde{C}_D)$, or for $C_D$ otherwise.

c) Let N(C) be the neighborhood of C, i.e. all vertices of the tooth model, which share an edge with C (i.e., which are referenced by a triangle on the tooth surface, which also references C).

From N(C), select a vertex C' with $C'_z=\max\{(M^T \cdot P)_z, P \in N(C)\}$, i.e. the neighboring point of C, which has the greatest z-coordinate (after applying the $M^T$ transformation defined above). If $C'_z \leq C_z$, this means that C is already a local maximum. In this case choose the other cusp (that means, now C will stand for $C_D$ if it stood for $C_M$ before and vice versa), and repeat step c). If both cusps are local maxima, then step 3) is finished; and go to step 4).

d) replace C by C' and go back to a).

Figure 27:
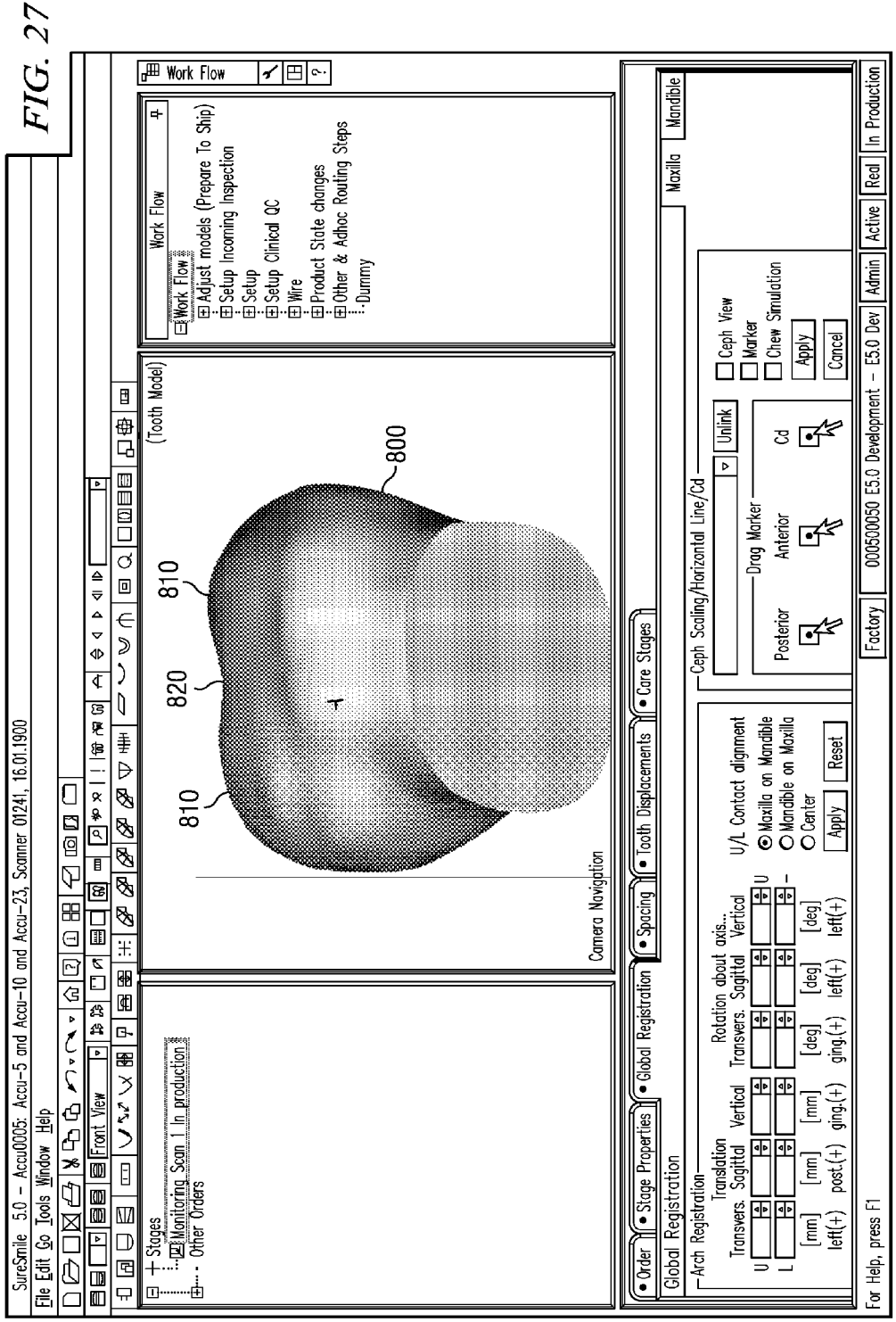
FIG. 27 shows a screen shot illustrating the tooth model, now from labial perspective, according to a preferred embodiment of the invention. Now the contours show two hills with a valley in between. The valley is the buccal groove.

FIG. 27 shows a screen shot illustrating the tooth model 800, now from labial perspective. Now the contours show two hills 810 with a valley 820 in between. The valley 820 is the buccal groove.

Figure 28:
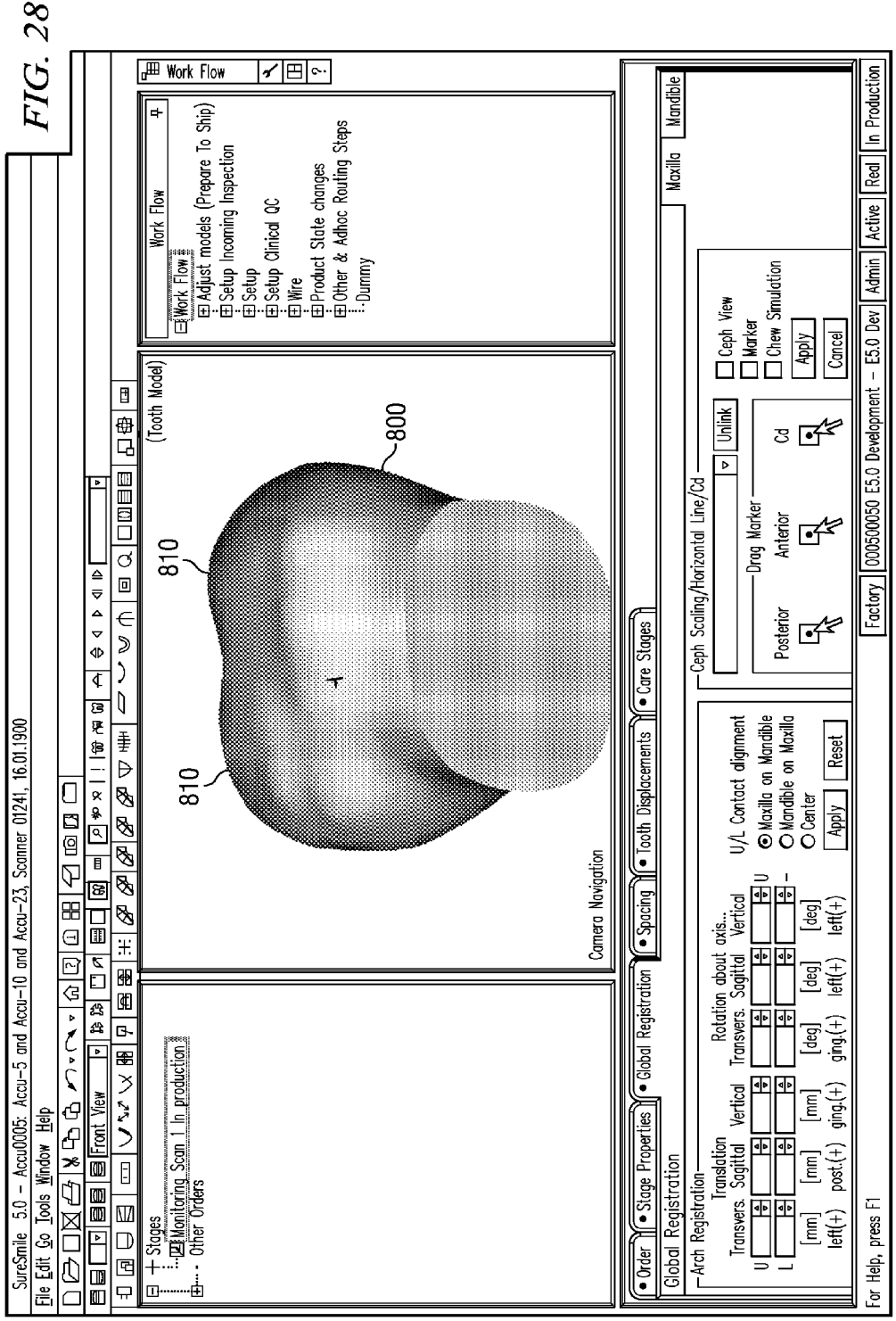
FIG. 28 shows a screen shot illustrating the tooth model after applying the second rotation, so that the two hills have the same height, according to a preferred embodiment of the invention.

FIG. 28 shows a screen shot illustrating the tooth model 800, after applying the second rotation, so that the two hills 810 have the same height.

Figure 29:
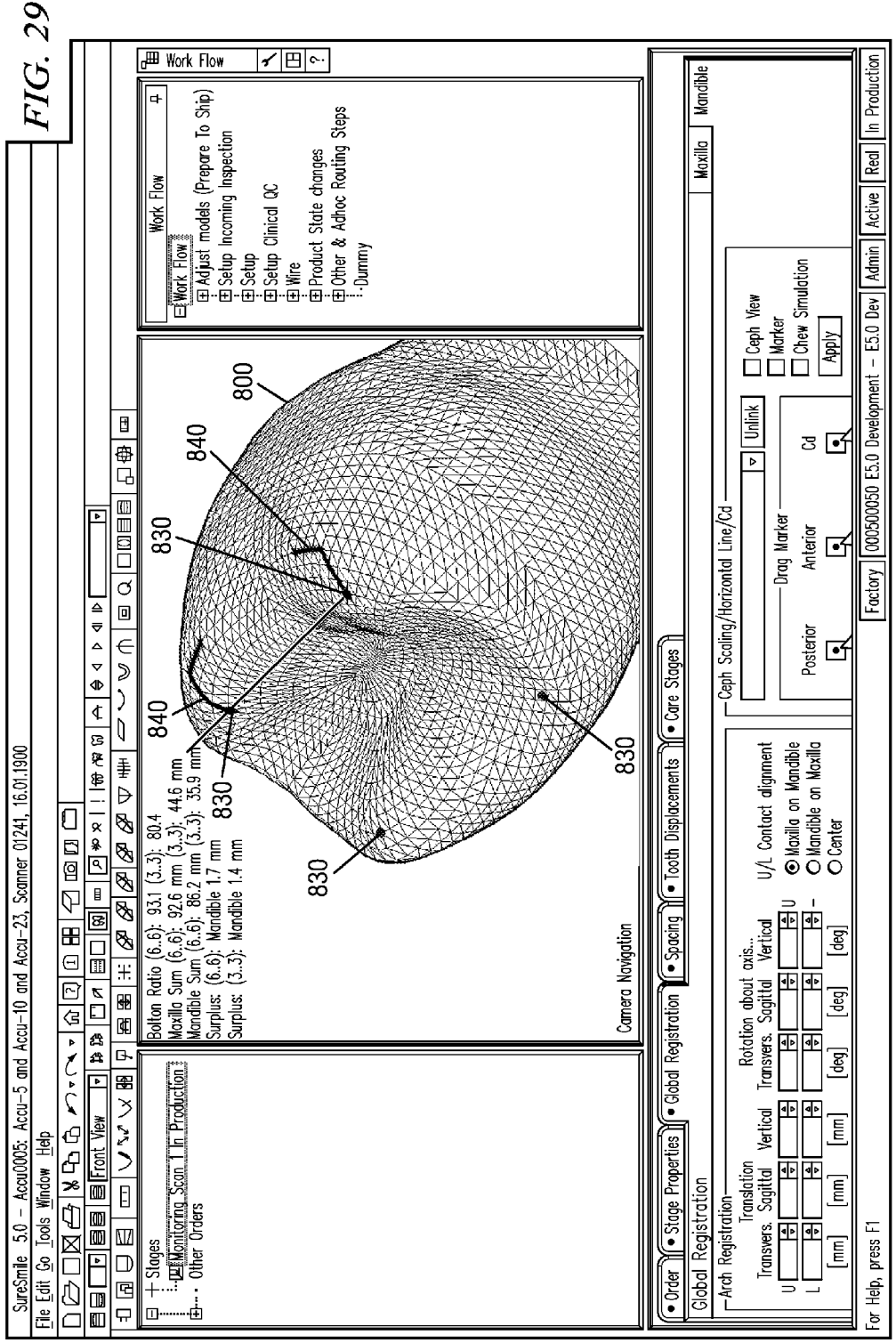
FIG. 29 shows a screen shot illustrating the tooth model with the cusp tips. The smooth lines show the way of the "moving" cusp tips, according to the preferred embodiment of the invention.

FIG. 29 shows a screen shot illustrating the tooth model 800 with the cusp tips 830. The smooth lines 840 show the way of the "moving" cusp tips. That is, the cusp tips are moved along the surface of the tooth, always along the edge of a triangle on the surface of the tooth, with the greatest increment of the z-coordinate, until a local maximum is reached, i.e. no more increment in the z-coordinate is possible.

Step 4. Find a "saddle-point" (the "lowest" vertex along the "highest" path from cusp to cusp):

Find a path $P_0, \ldots, P_n$, with:

i) $\forall i: P_i \in T$ (the path consists of vertices of the tooth model);

ii) $P_0 := C_M$ and $P_n := C_D$ (the path starts at one cusp tip, and ends at the other);

iii) $\forall i: P_{i+1} \in N(P_i)$ (each two consecutive points of the path are connected by an edge of the tooth model);

iv) $\forall i \in \{2, \ldots, n\}, \forall j \leq i-1: P_i \notin N(P_j)$ (this condition implies that the path contains no loops);

v) $\forall i \in \{1, \ldots, n\}: (P_i)_z = \max\{(M^T \cdot P)_z, P \in N(P_{i-1}) \wedge P \notin N(P_0) \wedge \ldots \wedge P \notin N(P_{i-2})\}$ (that means, always take the point with the greatest z-coordinate (after applying the transformation) of all vertices, which meet iii) and iv))

From this path, choose the vertex with the smallest z-coordinate, i.e. $S := P_{i'}$ with i' so, that $(P_{i'})_z = \min\{(M^T \cdot P_i)_z, i \in \{0, \ldots, n\}\}$.

Then, S is the buccal groove of the tooth model under consideration.

Figure 30:
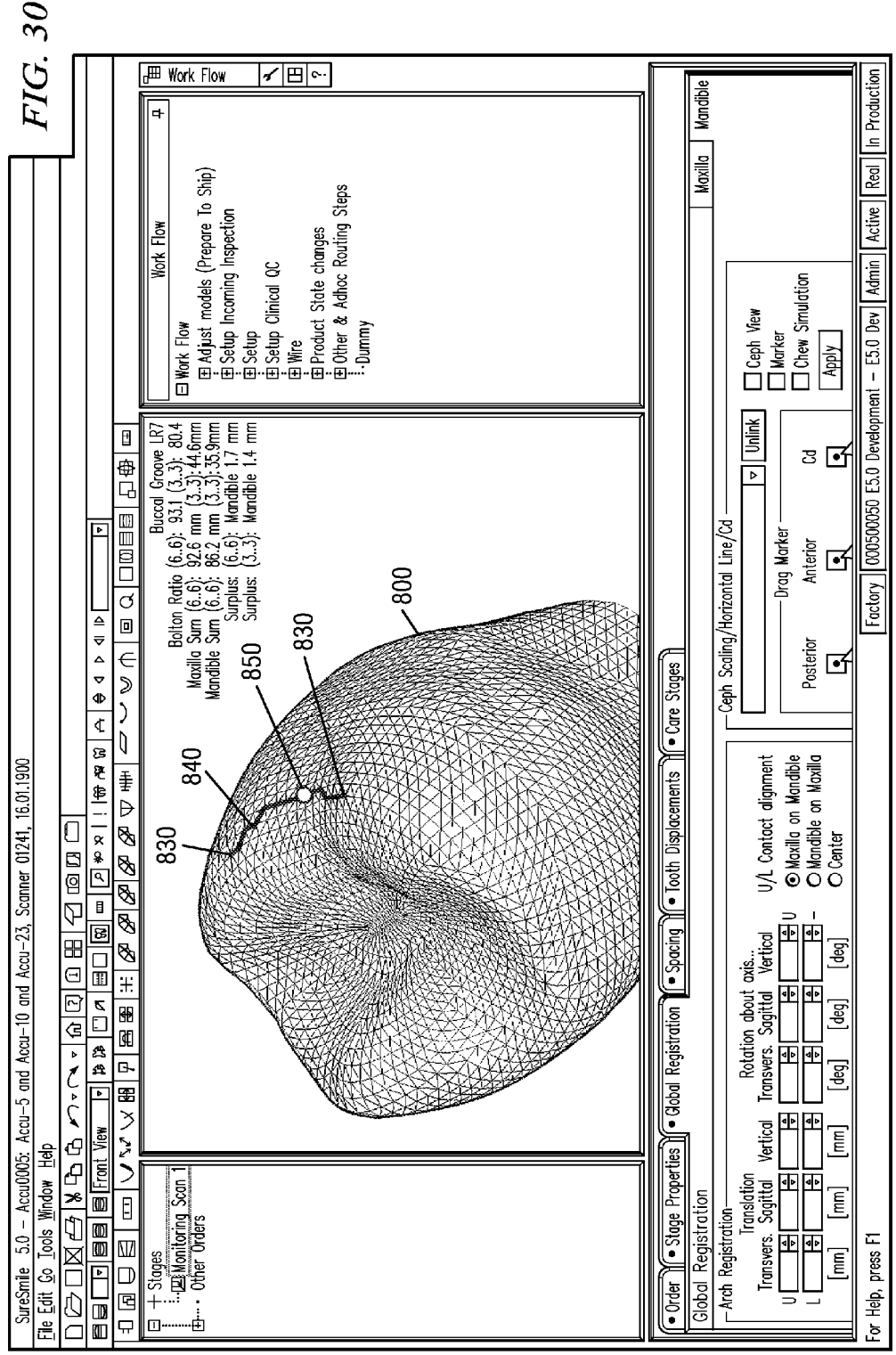
FIG. 30 shows a screen shot illustrating the virtual tooth model and the "saddle point", according to the preferred embodiment of the invention.

FIG. 30 shows a screen shot illustrating the tooth model 800 and the last part of the procedure, i.e. finding the "saddle point" 850. The path 840, which connects the "moved cusp tips" 830, located at the end-points of the path 840. The path 840 is the highest possible path, which connects the cusp tips 830. The lowest point along this path is the "saddle-point" 850, which is the buccal grove of the virtual tooth 800.

Figure 31:
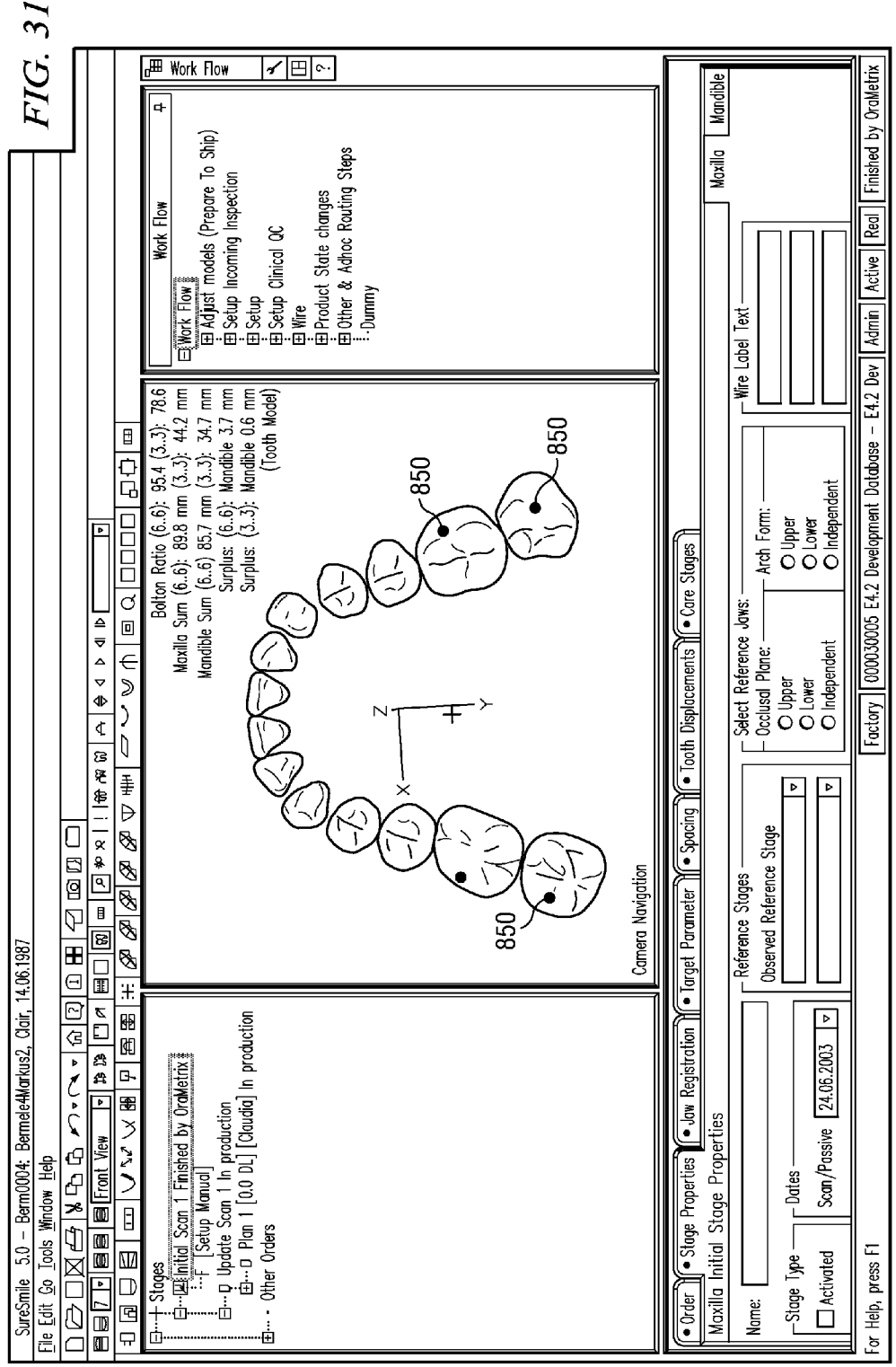
FIGS. 31 and 32 show screen shots illustrating several tooth models with buccal groves, according to the preferred embodiment of the invention.
Figure 32:
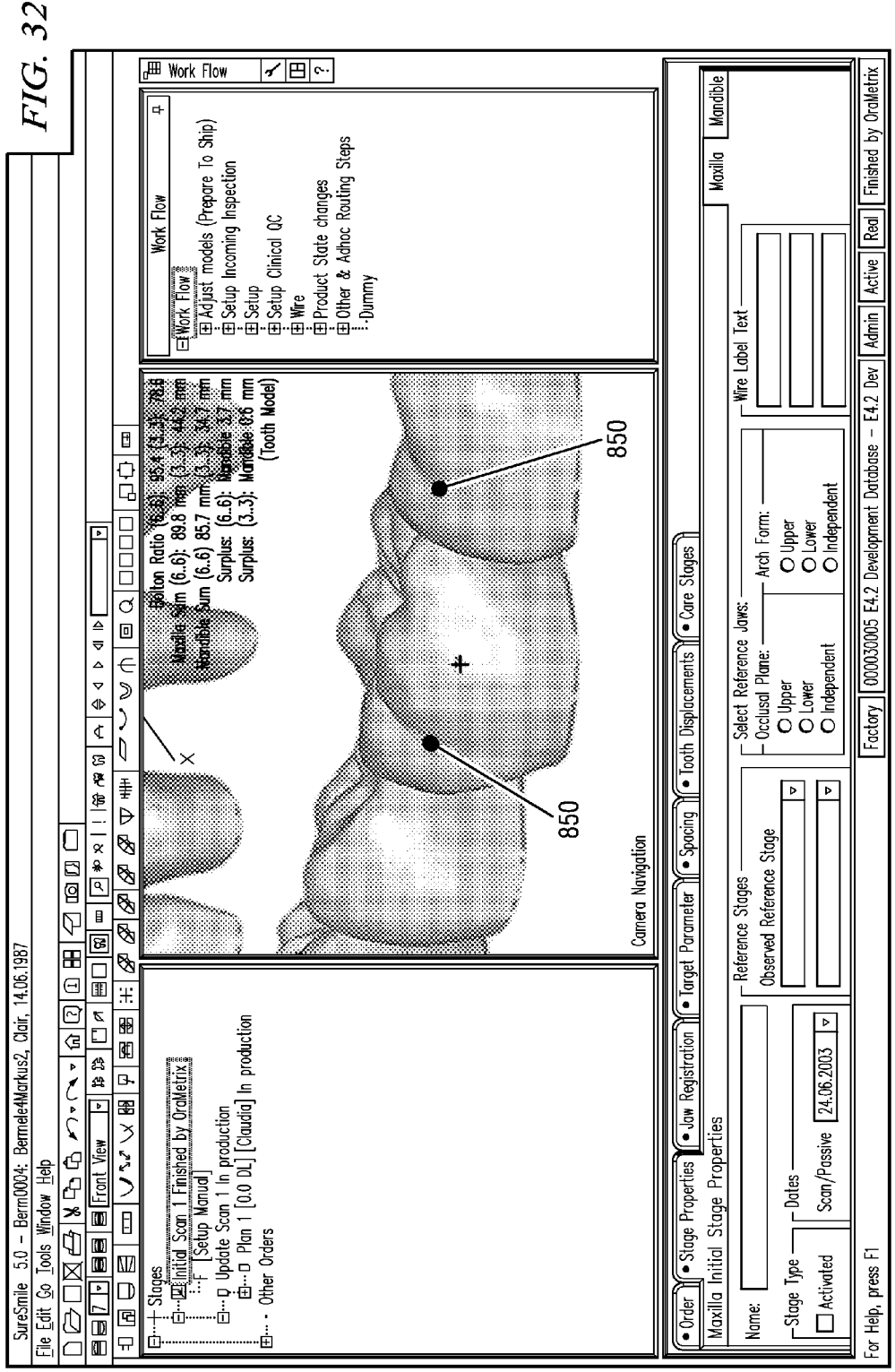

FIGS. 31 and 32 show a screen shots illustrating several tooth models with buccal groves 850.

Presently preferred and alternative embodiments of the invention have been set forth. Variation from the preferred and alternative embodiments may be made without departure from the scope and spirit of this invention.

We claim:

1. A method of finding ideal contact points on a tooth, comprising the steps of:
   (a) in-vivo scanning said tooth with a hand-held optical scanner by projecting frames of patterns on surface of said tooth and receiving reflected frames, wherein said reflected frames are reflected off of said surface of said tooth;
   (b) receiving said reflected frames in a workstation and creating a virtual three-dimensional model of said tooth by registering said reflected frames to each other using software instructions in said workstation;
   (c) defining a tooth axes system (TAS) for said virtual three-dimensional model of said tooth; wherein said TAS comprises an origin, an x-axis in the mesial and distal directions, a y-axis in the labial and lingual directions and a z-axis in the occlusal and gingival directions;
   (d) intersecting surface of said virtual model of said tooth with an x-y plane based up on said tooth axes system for said tooth; and
   (e) finding most mesial point and most distal point on said intersected surface of said virtual model of said tooth; whereby said most mesial point and said most distal point are two ideal contact points for said tooth.

2. The method of claim 1, wherein said most mesial point and said most distal point are points with lowest/highest x-coordinates.

3. A method of finding central groove of a tooth, wherein said tooth is a molar or a premolar, using a workstation, comprising the steps of:
   (a) in-vivo scanning said tooth with a hand-held optical scanner by projecting frames of patterns on surface of said tooth and receiving reflected frames, wherein said reflected frames are reflected off of said surface of said tooth;
   (b) receiving said reflected frames in a workstation and creating a virtual three-dimensional model of said tooth by registering said reflected frames to each other using software instructions in said workstation;
   (c) defining a tooth axes system (TAS) for said virtual three-dimensional model of said tooth; wherein said TAS comprises an origin, an x-axis in the mesial and distal directions, a y-axis in the labial and lingual directions and a z-axis in the occlusal and gingival directions;
   (d) determining most occlusal cusp tip on lingual side and most occlusal cusp tip on buccal side of said virtual three-dimensional model of said tooth;
   (e) rotating said tooth around x-axis of said tooth axes system for said tooth using a rotation matrix in a manner so that said most occlusal cusp tip on lingual side and said most occlusal cusp tip on buccal side both have same z-coordinates;
   (f) finding a series of deepest points on occlusal contour of said tooth surface by:
      i. creating a plane parallel to y-z-plane of said tooth axes system;
      ii. cutting all edges of surface of said tooth by said plane parallel to y-z-plane of said tooth axes system thereby forming a slice of said tooth surface;
      iii. finding deepest point on occlusal contour of said slice of said tooth surface;
      iv. moving said plane parallel to y-z-plane of said tooth axes system until entire surface said tooth is covered; and repeating steps ii and iii for each new position of said plane parallel to y-z-plane of said tooth axes system; and
   (g) finding a line having minimal average distance from said series of deepest points; whereby said line is defined as said central groove for said tooth.

4. The method of claim 3, wherein said most occlusal cusp tip is a point having highest z-coordinate.

5. The method of claim 3, further comprising the steps of:
   (d) identifying first end-point and second end-point of said line having minimal average distance from said series of deepest points;
   (e) constructing first line-segment parallel to said z-axis of said tooth axes system for said tooth starting from said first end-point and ending on first point on said surface of said tooth wherein said first point is most occlusal point; and
   (f) constructing second line-segment parallel to said z-axis of said tooth axes system for said tooth starting from said second end-point and ending on second point on said surface of said tooth wherein said second point is most occlusal point;
   whereby said first point and said second point represent said central grove on said surface of said tooth.

6. A method of finding buccal groove of a tooth, wherein said tooth is a molar, comprising the steps of:
   (a) in-vivo scanning said tooth with a hand-held optical scanner by projecting frames of patterns on surface of said tooth and receiving reflected frames, wherein said reflected frames are reflected off of said surface of said tooth;
   (b) receiving said reflected frames in a workstation and creating a virtual three-dimensional model of said tooth by registering said reflected frames to each other using software instructions in said workstation;
   (c) defining a tooth axes system (TAS) for said virtual three-dimensional model of said tooth; wherein said TAS comprises an origin, an x-axis in the mesial and distal directions, a y-axis in the labial and lingual directions and a z-axis in the occlusal and gingival directions;
   (d) determining mesial labial cusp tip and distal labial cusp tip of said virtual three-dimensional model of said tooth;
   (e) finding first vertex closest to said mesial labial cusp tip and second vertex closest to said distal labial cusp tip on surface of said virtual three-dimensional model of said tooth;
   (f) rotating said virtual three-dimensional model of said tooth around x-axis of said tooth based upon tooth axes system for said tooth lingually by 60°;
   (g) performing steps (i) to (iv);
      (i) rotating said virtual three-dimensional model of said tooth around an axis orthogonal to z-axis of said tooth based upon tooth axes system for said tooth and vector connecting said mesial labial cusp tip and said distal labial cusp tip in a manner such that said mesial labial cusp tip and said distal labial cusp tip have same z-coordinates;
      (ii) choosing one of said two cusp tips, which has been moved less up to now (or any, if they have been moved equally);
      (iii) moving said chosen cusp tip along said surface of said tooth until said cusp tip is on local maxima;
      (iv) repeating steps (i)-(iii) until said both cusp tips are at local maxima; and
   finding a saddle-point, wherein said saddle-point is lowest vertex along highest path from said mesial labial cusp tip to said distal labial cusp tip; whereby said saddle-point is defined as said buccal groove of said tooth.

* * * * *